(12) United States Patent
He et al.

(10) Patent No.: US 8,900,522 B2
(45) Date of Patent: Dec. 2, 2014

(54) ETHYLENE CRACKING FURNACE WITH MULTI-PASS RADIANT COIL

(75) Inventors: Xiou He, Beijing (CN); Changli Li, Beijing (CN); Zhaobin Zhang, Beijing (CN); Jingkun Liu, Beijing (CN); Mujun Yuan, Beijing (CN); Cong Zhou, Beijing (CN); Yuping Guo, Beijing (CN); Yonghua Zhao, Beijing (CN); Hainü Shen, Beijing (CN)

(73) Assignees: China Petroleum & Chemical Corporation, Beijing (CN); SINOPEC Engineering Incorporation, Beijing (CN); China Petroleum & Chemical Corporation, Beijing Institute of Chemical Industry, Beijing (CN)

( * ) Notice: Subject to any disclaimer, the term of this patent is extended or adjusted under 35 U.S.C. 154(b) by 424 days.

(21) Appl. No.: 13/504,117

(22) PCT Filed: Oct. 26, 2010

(86) PCT No.: PCT/CN2010/000170
§ 371 (c)(1),
(2), (4) Date: Apr. 25, 2012

(87) PCT Pub. No.: WO2011/050573
PCT Pub. Date: May 5, 2011

(65) Prior Publication Data
US 2012/0219466 A1 Aug. 30, 2012

(30) Foreign Application Priority Data

Oct. 27, 2009 (CN) .......................... 2009 1 0181016

(51) Int. Cl.
*F28D 7/00* (2006.01)
*C10G 9/14* (2006.01)
*C07C 4/04* (2006.01)

(52) U.S. Cl.
CPC .............. *C07C 4/04* (2013.01); *C10G 2400/20* (2013.01)
USPC ........... 422/198; 422/200; 196/110; 196/116; 165/177; 165/183; 122/240.1

(58) Field of Classification Search
USPC ........ 422/198, 200; 165/177, 183; 122/240.1; 196/110, 116
See application file for complete search history.

(56) References Cited

U.S. PATENT DOCUMENTS 2,557,569 A * 6/1951 Schutt ........................... 196/110

(Continued)

FOREIGN PATENT DOCUMENTS

| CN | 1050535 A | 4/1991 |
|---|---|---|
| CN | 2816045 Y | 9/2006 |
| CN | 101062883 A | 10/2007 |

(Continued)

*Primary Examiner* — Walter D Griffin
*Assistant Examiner* — Huy-Tram Nguyen
(74) *Attorney, Agent, or Firm* — Novick, Kim & Lee, PLLC; Allen Xue

(57) ABSTRACT

The invention relates to an ethylene cracking furnace having a multi-pass radiant coil, comprising at least one radiant section. In the radiant section there are provided with bottom burners and/or sidewall burners, and at least one set of multi-pass radiant coil longitudinally arranged in the radiant section. The multi-pass radiant coil is a four- to ten-pass type radiant coil. At least one tube of the multi-pass radiant coil is arranged to be spatially adjacent to a tube which is not consecutive to said at least one tube. With this arrangement, the thermal radiation influence between tubes with high temperature can be reduced, so that the tubes with low temperature can absorb the radiation heat from the tubes with high temperature. Therefore, the surface temperature of the tubes with high temperature can be reduced, thus extending the lifetime of the radiant coil and the operational cycle of the cracking furnace.

16 Claims, 21 Drawing Sheets

(56) References Cited

U.S. PATENT DOCUMENTS

| | | | |
|---|---|---|---|
| 3,407,789 A * | 10/1968 | Hallee et al. | 122/356 |
| 6,419,885 B1 * | 7/2002 | Di Nicolantonio et al. | 422/198 |
| 6,528,027 B1 * | 3/2003 | Brewer et al. | 422/200 |
| 6,719,953 B2 * | 4/2004 | Di Nicolantonio et al. | 422/198 |
| 2008/0142411 A1 * | 6/2008 | Barendregt et al. | 208/132 |

FOREIGN PATENT DOCUMENTS

| | | |
|---|---|---|
| CN | 101333147 A | 12/2008 |
| CN | 201276507 Y | 7/2009 |
| CN | 201520747 U | 7/2010 |
| JP | H07238288 A | 9/1995 |
| WO | 2005068926 A1 | 7/2005 |

* cited by examiner

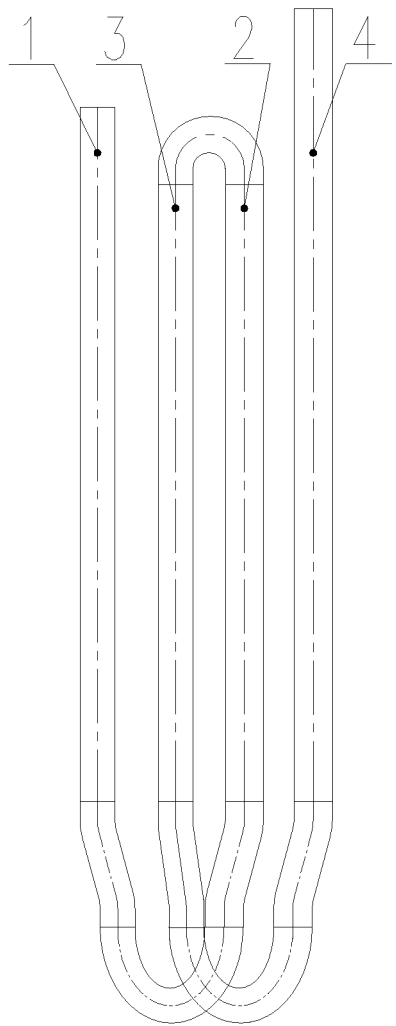
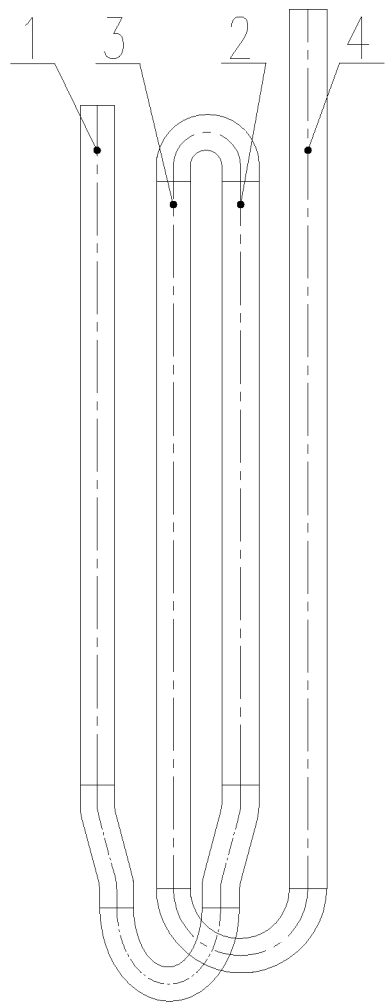
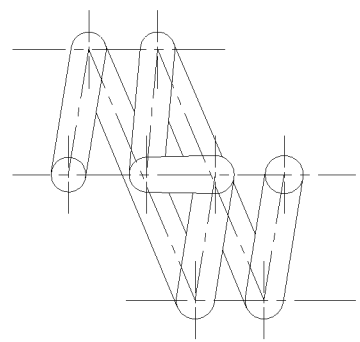
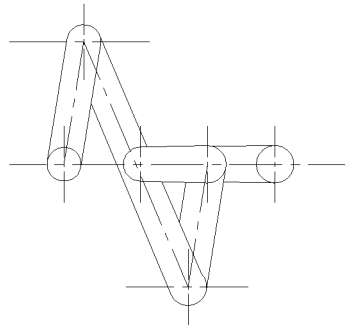
Fig. 4                  Fig. 5

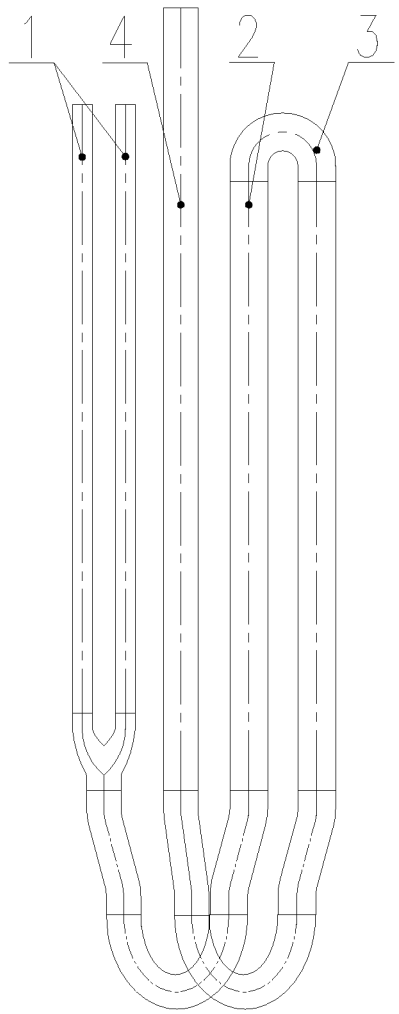 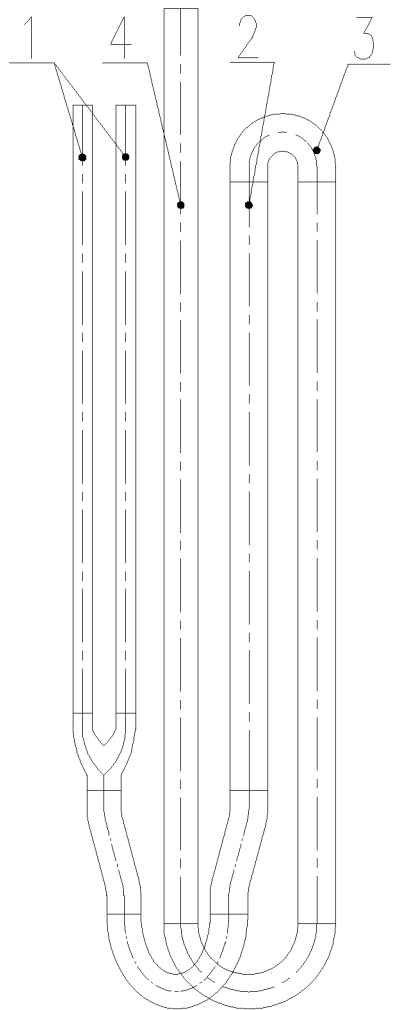
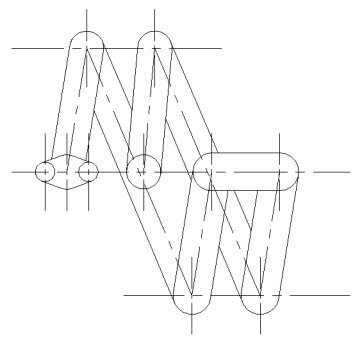 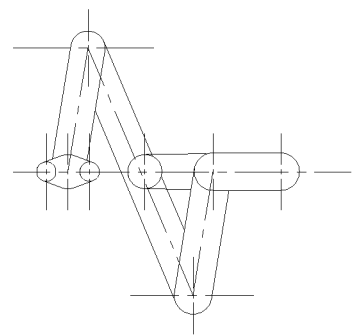
Fig. 6                                         Fig. 7

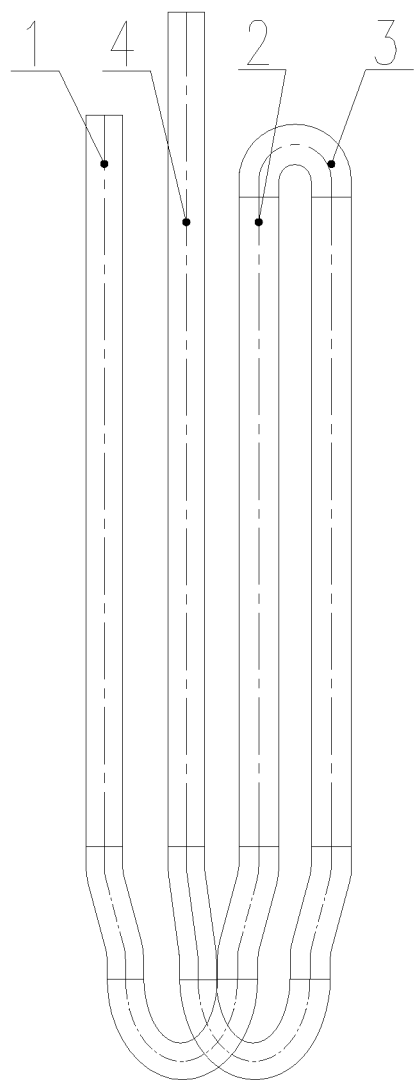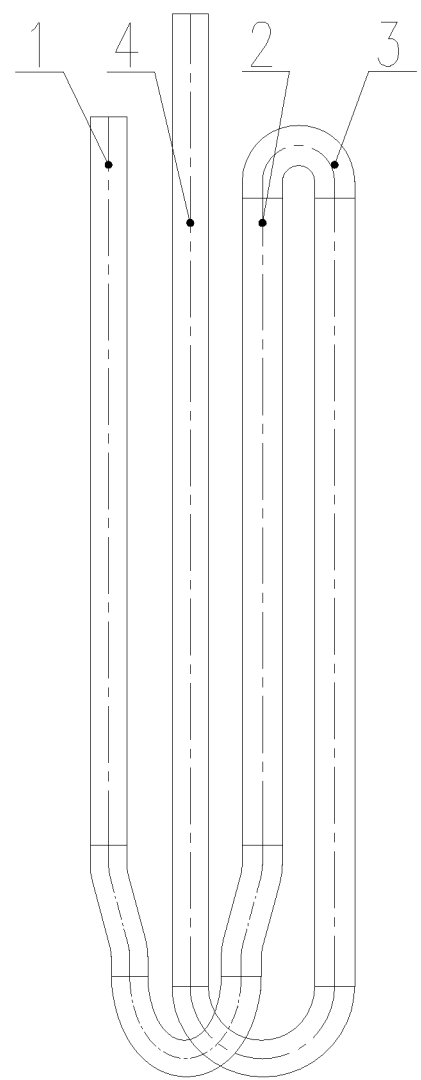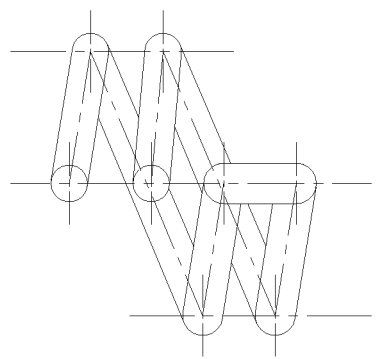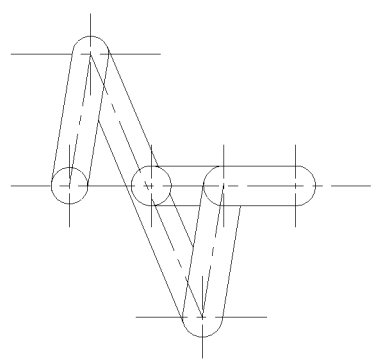
Fig. 8              Fig. 9

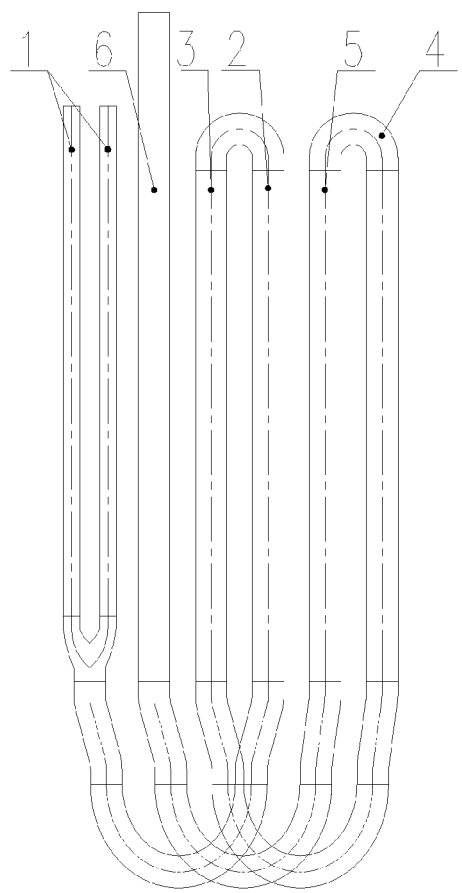
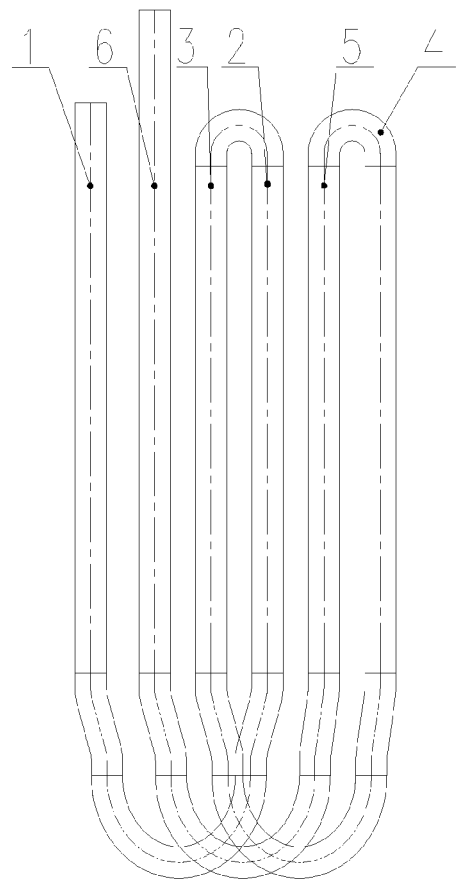
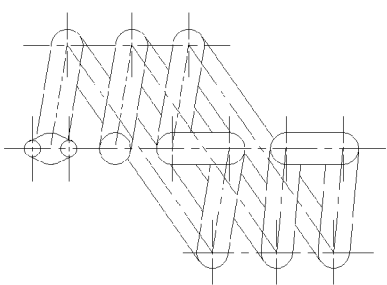
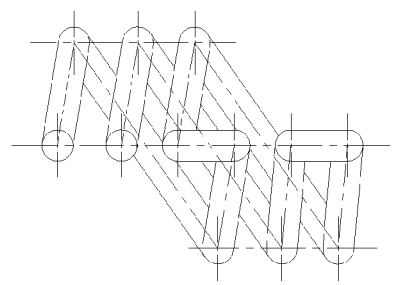
Fig. 14        Fig. 15

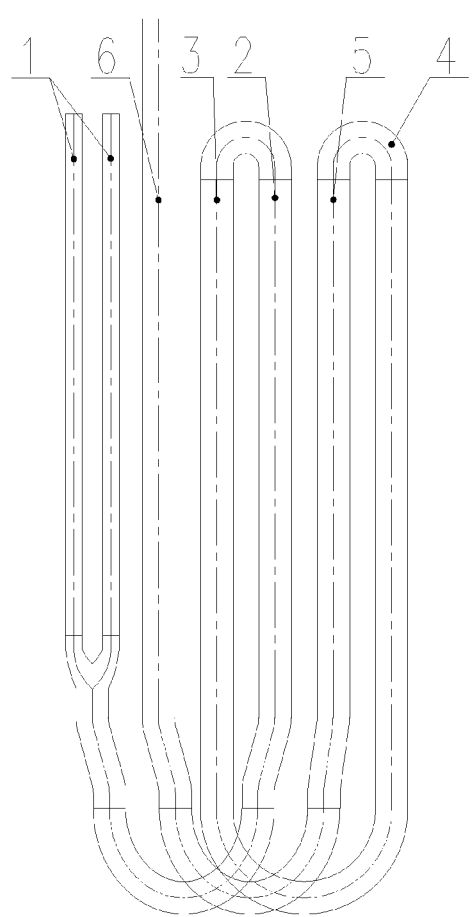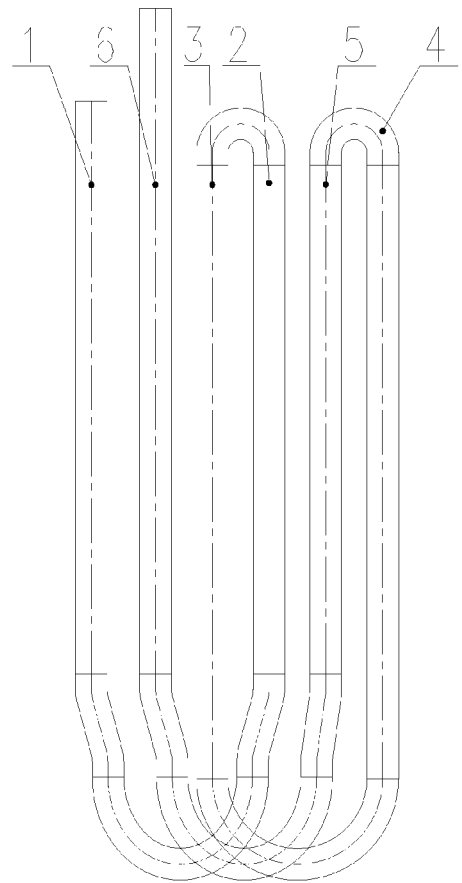
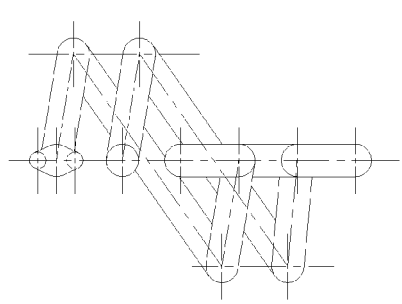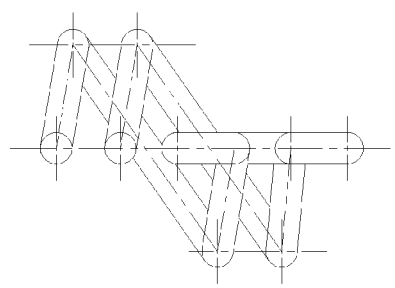
Fig. 16                    Fig. 17

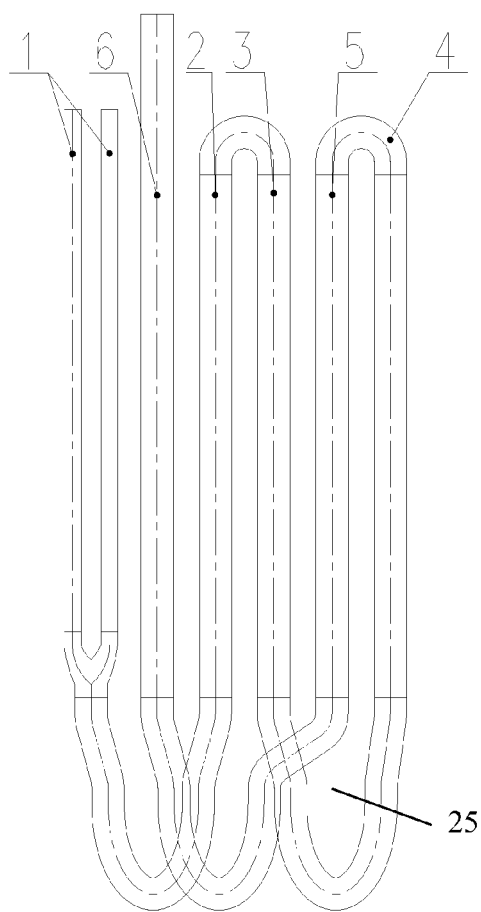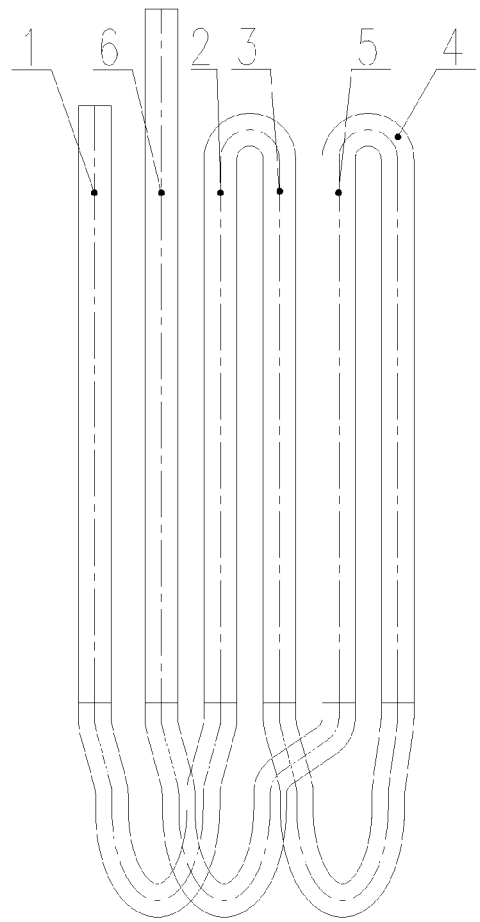
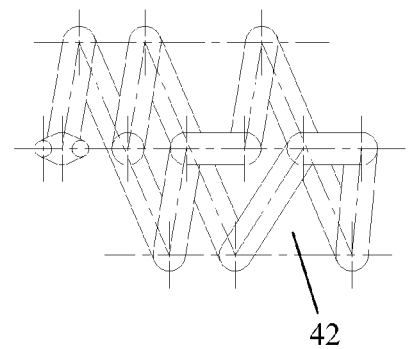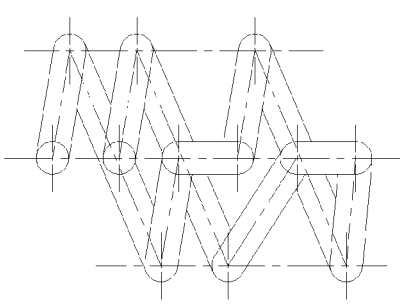
Fig. 18　　　　　　　　　　　　　　Fig. 19

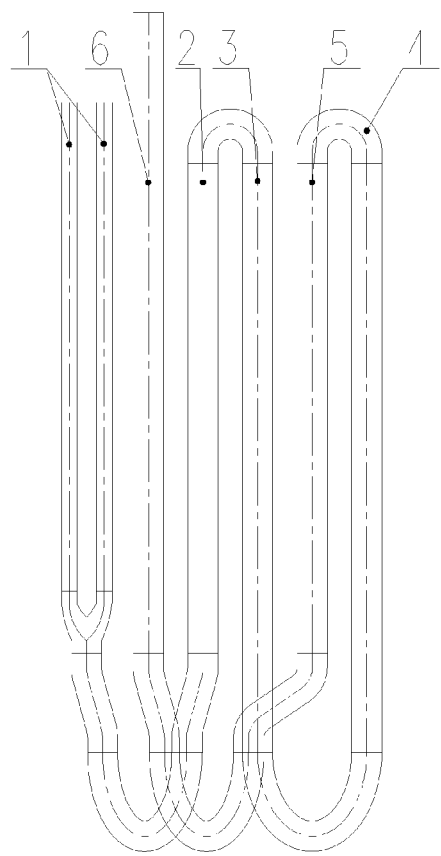
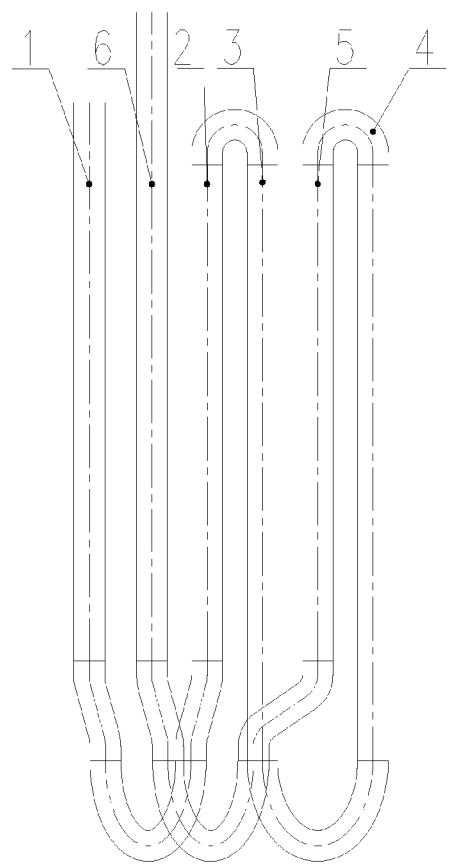
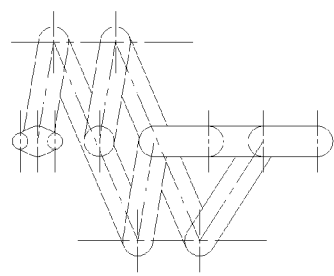
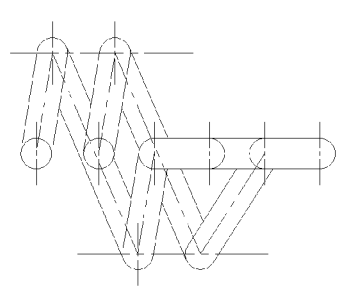
Fig. 20　　　　　　　　Fig. 21

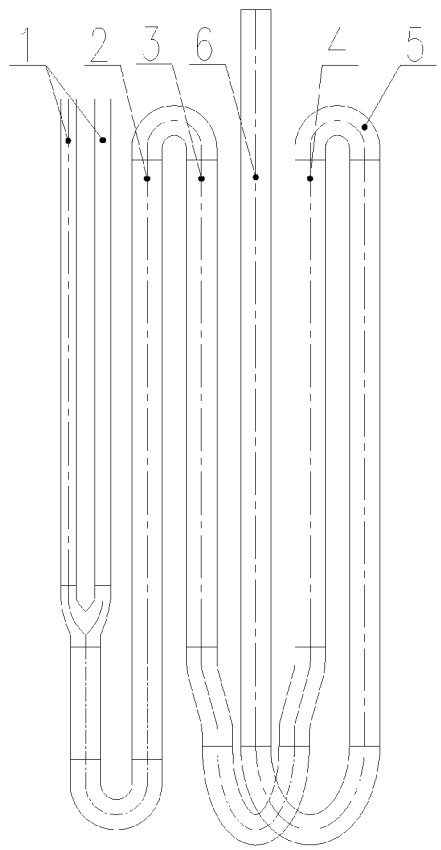
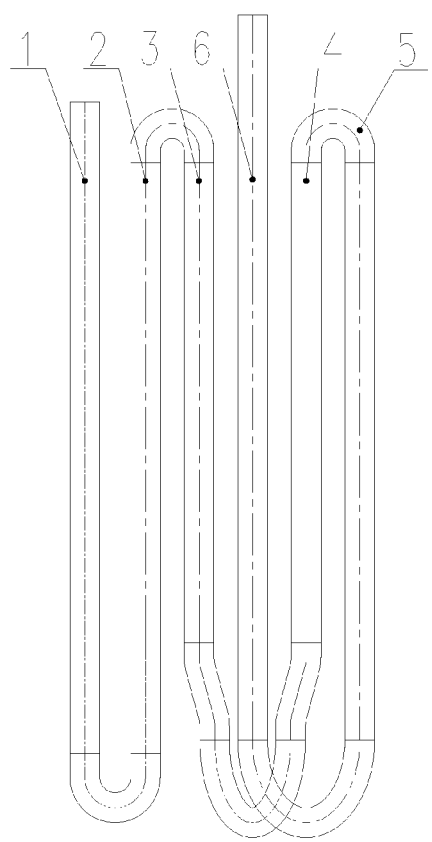
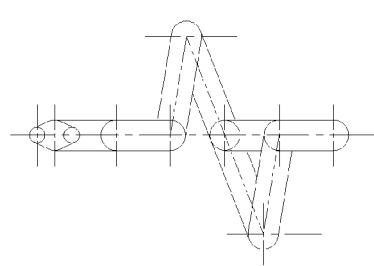
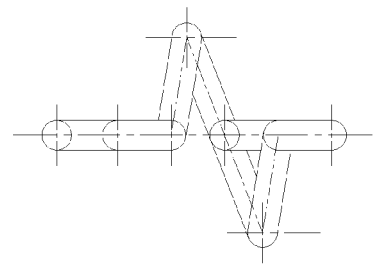
Fig. 24                    Fig. 25

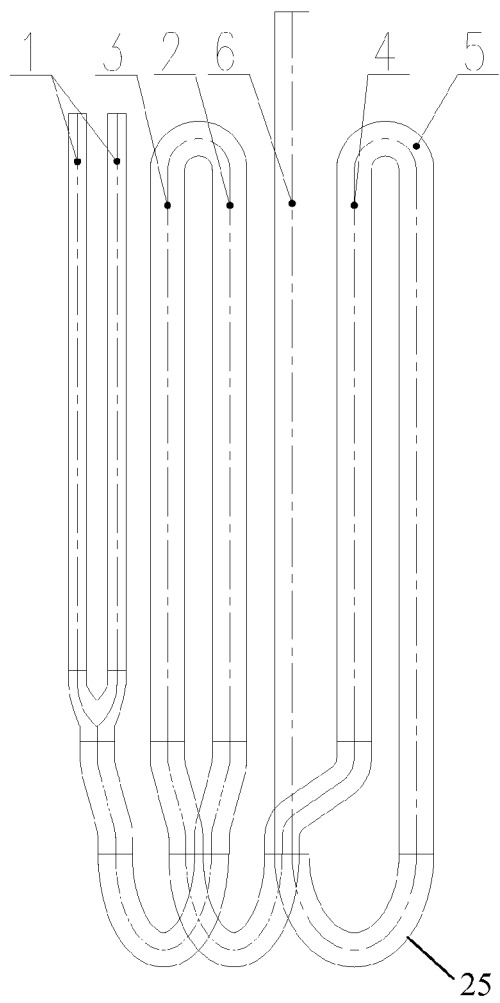
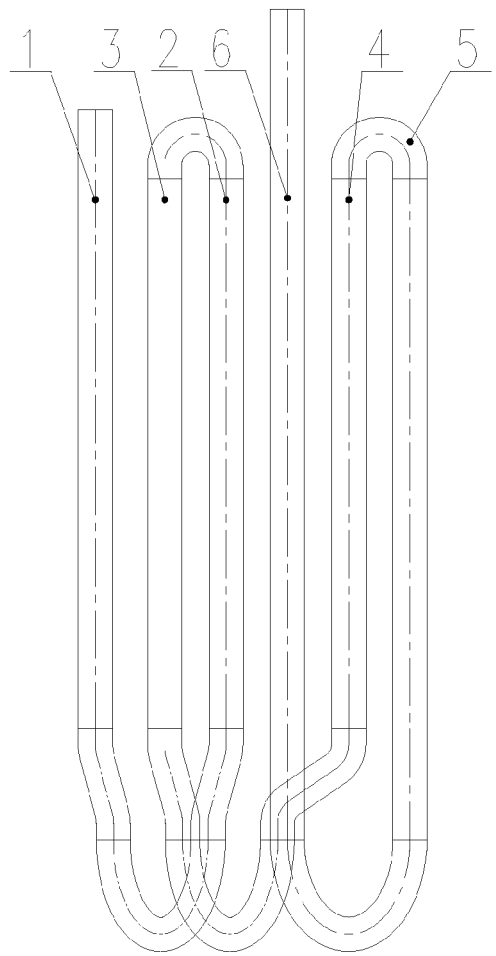
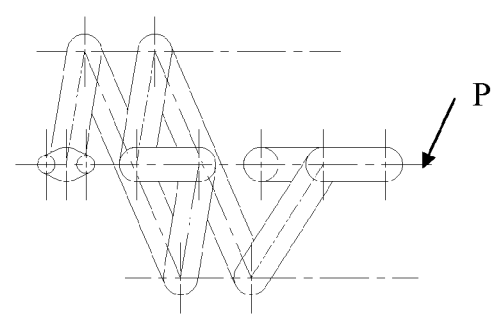
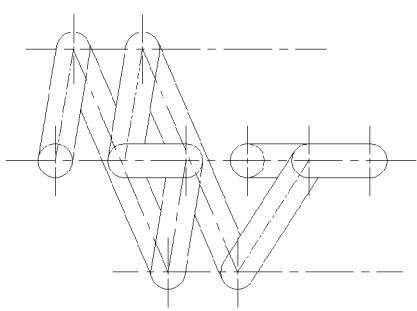
Fig. 28　　　　　　　　　　　　　　　Fig. 29

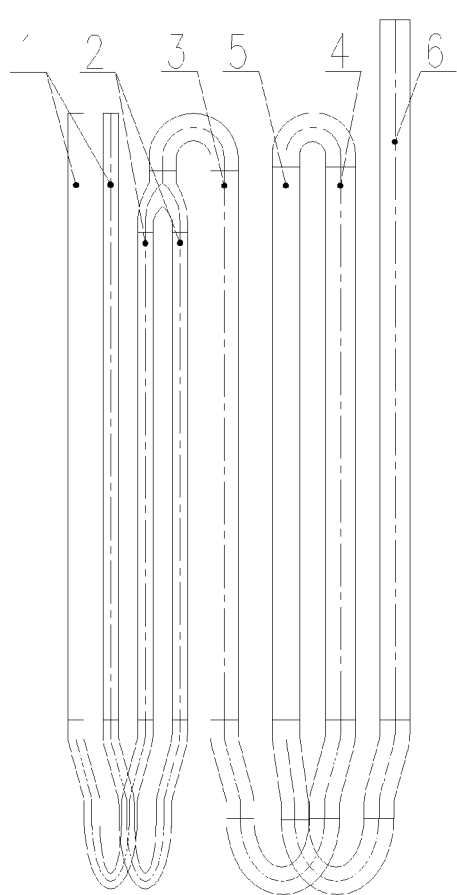
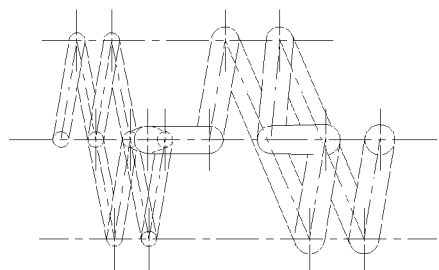
Fig. 30
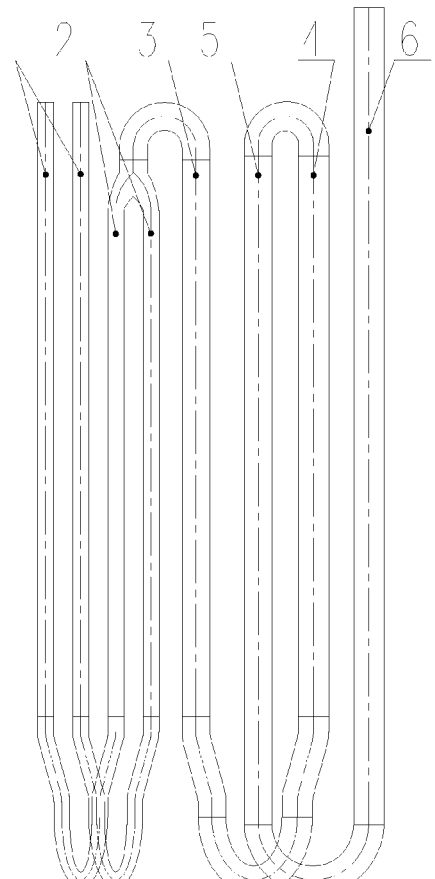
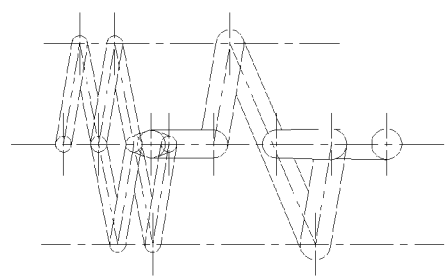
Fig. 31

ETHYLENE CRACKING FURNACE WITH MULTI-PASS RADIANT COIL

CROSS-REFERENCE TO RELATED APPLICATIONS

This application is. a U.S. national stage application of International application No. PCT/CN2010/001703, filed on Oct. 26, 2010 and entitled "ETHYLENE CRACKING FURNACE WITH MULTI-PASS RADIANT COIL, " which in turn claims priority to Chinese Patent Application No. 200910181016.6 , filed on Oct. 27, 2009 and entitled "ETHYLENE CRACKING FURNACE WITH MULTI-PASS RADIANT COIL," each of which is hereby incorpotated by reference in its entirety.

TECHNICAL FIELD

The present invention relates to petrochemical engineering field, and more specifically, to the radiant coil structure of an ethylene cracking furnace used in petrochemical engineering.

BACKGROUND

The ethylene cracking techniques used in petrochemical ethylene equipments mainly include those developed by LUMMUS Co. (USA), Stone & Webster Co. (USA), Kellog & Braun Root Co. (USA), Linde Co. (Germany), Technip KTI Co. (Netherlands), and the CBL cracking furnace developed by China Petrochemical Corporation.

FIG. 1A shows a typical ethylene cracking furnace 10, which comprises a radiant section 11, a convective section 13, and a flue section 12 located between the radiant section 11 and the convective section 13. Within the radiant section 11 a set of multi-pass radiant coil 14 is provided in the central plane P of the radiant section 11 along the longitudinal direction thereof In addition, the radiant section 11 is further provided with bottom burners 15 and/or side burners 16 for heating. Moreover, the ethylene cracking furnace 10 further comprises a transfer line exchanger 17, a high-pressure steam drum 18 and an induced draft fan 19, etc. Nowadays, in most companies a four- to six-pass (~60 meter) medium-selectivity radiant coil with or without branches of variable diameters is used and the residence time thereof is controlled within the range of 0.4 to 1.0 second, so that the radiant coil suitable for cracking gas material can be also adapted for liquid material, with a proper operation cycle and a satisfied material adaptability. The first tube or the first two tubes of the radiant coil are of small diameter. Therefore, a quick temperature rise can be achieved since the specific surface area of the small-diameter tubes is relatively large. The tubes following the second tube are of large diameter, in order to reduce the influences on coking sensitivity. The four-pass medium-selectivity radiant coil used can be configured as 4-2-1-1 type, 2-2-1-1 type, 1-1-1-1 type and 2-1-1-1 type, etc.

For the radiant coil 14 of the prior arts, all tubes thereof are generally spatially arranged in sequence along the flow direction of fluid. In the meantime, the tubes are connected to each other with common elbows.

FIG. 1B shows a typical arrangement of multi-pass radiant coil of an ethylene cracking furnace in the prior art. As shown in FIG. 1B, the multi-pass radiant coil 30 is a four-pass radiant coil, comprising the first tube 1, the second tube 2, the third tube 3 and the fourth tube 4 along the fluid flow direction (i.e., from left to right in the drawing). The first tube 1 is a Y-shaped branched tube with varied diameters. All the four tubes are spatially arranged in sequence, i.e., the second tube 2 being arranged spatially between the first tube 1 and the third tube 2, and the third tube 3 being arranged spatially between the second tube 2 and the fourth tube 4, and so on. That is to say, each tube is arranged spatially adjacent to the one or two tubes that are consecutive to said tube. In addition, the tubes are connected to each other by means of common elbows 35. FIG. 1B further shows all tubes and the elbows are located in one single plane, i.e., the central plane P of the radiant section.

In this typical arrangement, the tubes are spatially arranged in sequence. Since the fluid flows along the multi-pass radiant coil from the first tube to the second tube, then to the third tube and finally to the fourth tube, the tube wall temperature of these tubes is gradually increased in this order. In other words, the temperature of the first, second, third and fourth tubes is gradually increased in this order. Therefore, an uneven temperature distribution is generated in the radiant section. Moreover, radiant heat exchange will also exist between the high-temperature tubes, i.e., the third and the fourth tubes in this case, which would negatively influence on reducing the tube wall temperature and extending the operation cycle of the furnace.

Furthermore, in the multi-pass radiant coil of the prior arts, the tubes are connected to each other by means of common elbows. This is undesirable for absorption of heat expansion generated in each of these tubes. In a long time operation, it will easily lead to bending of tubes, lowering the lifetime of the radiant coil and therefore shortening the operation cycle thereof.

SUMMARY OF THE INVENTION

Considering the defects in the prior arts, the present invention aims to provide an ethylene cracking furnace having a multi-pass radiant coil, which includes a novel tube arrangement that can improve the heating condition so as to enable the tubes being heated more evenly. In addition, the present invention further aims to provide an ethylene cracking furnace having a multi-pass radiant coil, which can enhance the mechanical properties of the radiant coil, increase the on-line percentage of the cracking furnace, reduce the operation cost, and extend the lifetime of the coil and the operational cycle of the cracking furnace.

According to the present invention, an ethylene cracking furnace having a multi-pass radiant coil is provided, comprising at least one radiant section. In the radiant section there are provided with bottom burners and/or sidewall burners, and at least one set of multi-pass radiant coil longitudinally arranged in the radiant section; wherein the multi-pass radiant coil is a four- to ten-pass type radiant coil. At least one tube of the multi-pass radiant coil is arranged to be spatially adjacent to a tube which is not consecutive to said at least one tube.

It should be noted that with regard to the first tube, the tube consecutive thereto is the second tube; with regard to the second tube, the tubes consecutive thereto are the first tube and the third tube, and so on. With at least one tube of the multi-pass radiant coil being arranged to be spatially adjacent to a tube which is not consecutive to the at least one tube, said at least one tube can be spatially adjacent to a tube having a temperature not close to that of said at least one tube. Therefore, the even temperature distribution within the radiant section can be effectively improved. Consequently, the surface temperature of the radiant coil can be lowered, and thus the lifetime of the radiant coil and the operational cycle of the cracking furnace can both be extended.

According to an embodiment of the present invention, the last two tubes of the multi-pass radiant coil are arranged to be spatially non-adjacent to each other. Since the last two tubes have the highest temperatures among all tubes, the thermal radiation influence from the high-temperature tubes can be effectively reduced. Therefore, the surface temperature of the radiant coil can be further lowered, and thus both the lifetime of the radiant coil and the operational cycle of the cracking furnace can be further extended.

According to another embodiment of the present invention, the first tube and the last tube are arranged at the opposite outer sides of the whole multi-pass radiant coil respectively. Alternatively, in one example, at least one of the first tube and the last tube of the multi-pass radiant coil is not arranged at the opposite outer sides of the whole multi-pass radiant coil, but in the middle thereof.

According to one embodiment of the present invention, the tubes of the multi-pass radiant coil are connected with each other by means of connectors. Since the temperatures on the walls of the tubes in the multi-pass radiant coil are different from each other, the thermal expansion between two adjacent tubes will be different, thus resulting in thermal stress. In one example, at least one connector located in the lower part of the radiant section is a combined connector consisting of a U-shaped elbow and two S-shaped elbows located at the opposite sides of the U-shaped elbow respectively. With the above combined connector consisting of S-shaped elbows and U-shaped elbow, the thermal stress generated from heating and uneven burning at the opposite outer sides of the coil can be absorbed. Accordingly, tube bending due to the thermal stress resulted from any possible reasons can be prevented. In this way, the mechanical properties of radiant coil are effectively improved. Consequently, partial overheating due to tube bending can be avoided, and thus both of the lifetime of the radiant coil and the operational cycle of the cracking furnace can be extended.

In one example, the tubes in the central plane of the radiant section are arranged as not being spatially adjacent to each other, and at both sides of the central plane there are provided with equal quantity of S-shaped elbows connected by a U-shaped elbow. In such an arrangement, the temperature in the radiant section is more evenly distributed, and the distortion caused by thermal stress can be more evenly absorbed. These S-shaped elbows have downward projections parallel to each other, or at least one of them has a downward projection is not parallel to downward projections of the others due to structural requirements. Likewise, all U-shaped elbows can also have downward projections parallel to each other. These arrangements are advantageous for obtaining a very compact structure.

In all of the above embodiments, the combined connectors, consisting of S-shaped elbows and U-shaped elbow, for connecting the tubes in the lower part of the radiant section, form a profile of a closed, symmetrical and continuous curve in the side view, which will be described below in details with reference to FIGS. 32-35. The U-shaped elbow may be formed in various forms.

Furthermore, some conventional elbows which are not in form of the above-mentioned combined connectors can be placed in the central plane of the radiant section. These arrangements will be advantageous for obtaining a compact structure. As required in particular processes, the first tube can be a branched tube with varied diameters, or both of the first and the second tubes are branched tubes with varied diameters.

The present invention presents the following advantages over the prior arts: (i) since the high-temperature tubes and the low-temperature tubes are arranged alternately or in a form of partial interleaving arrangement, the heat radiation influence from the high-temperature tubes can be reduced, and the tubes with low temperature can absorb the heat from those with high temperature; as a result, the temperature of surface of the high-temperature tubes can be lowered, and both of the lifetime of the radiant coil and the operational cycle of the cracking furnace can be extended; and (ii) by using combined connectors other than common elbows to connect the bottoms of the tubes, the mechanical properties of the radiant coil can be significantly improved, which is advantageous for absorbing thermal stress generated by temperature differences between two adjacent tubes, thus preventing the tubes from bending due to the thermal stress, avoiding partial overheating due to tube bending, and eventually extending both the operation cycle of the cracking furnace and the lifetime of the radiant coil.

BRIEF DESCRIPTION OF DRAWINGS

FIGS. 2 to 9 show eight embodiments of four-pass radiant coil of an ethylene cracking furnace according to the present invention, respectively.

FIGS. 10 to 31 show twenty-two embodiments of six-pass radiant coil of an ethylene cracking furnace according to the present invention, respectively.

In each drawing, the same or similar reference number indicates the same component or structure.

It should be noted that each connector for connecting the tubes in the lower part of the radiant section respectively shown in FIGS. 2-31 similarly forms a profile of continuous curve in the side view, although not shown. That is to say, the side views of the combined connectors in these figures are similar to those of in FIGS. 32-35 (i.e., the lower portions of FIGS. 32-35)

DETAILED DESCRIPTION OF THE INVENTION

In the following the present invention will be discussed in details with reference to the accompanying drawings. It should be noted that the present invention aims to provide improvements on radiant coil in the radiant section of the ethylene cracking furnace. Other structures in the ethylene cracking furnace, such as the convective section, the transfer line exchanger and the like, are already known in the prior art. For example, the transfer line exchanger suitable for the present invention can be double-coil transfer line exchanger (such as linear transfer line exchanger, U-type transfer line exchanger and the first level of two-level transfer line exchanger, etc.), conventional boiler, bath boiler or quick transfer line exchanger. Moreover, the radiant coil of the present invention can be suitable for cracking gas material and liquid material, and can be used in building new cracking furnaces or reconstructing existing cracking furnaces. These are known to one ordinarily skilled in the art, and thus their details thereof are omitted here.

Four-Pass Radiant Coil

Figure 1A:
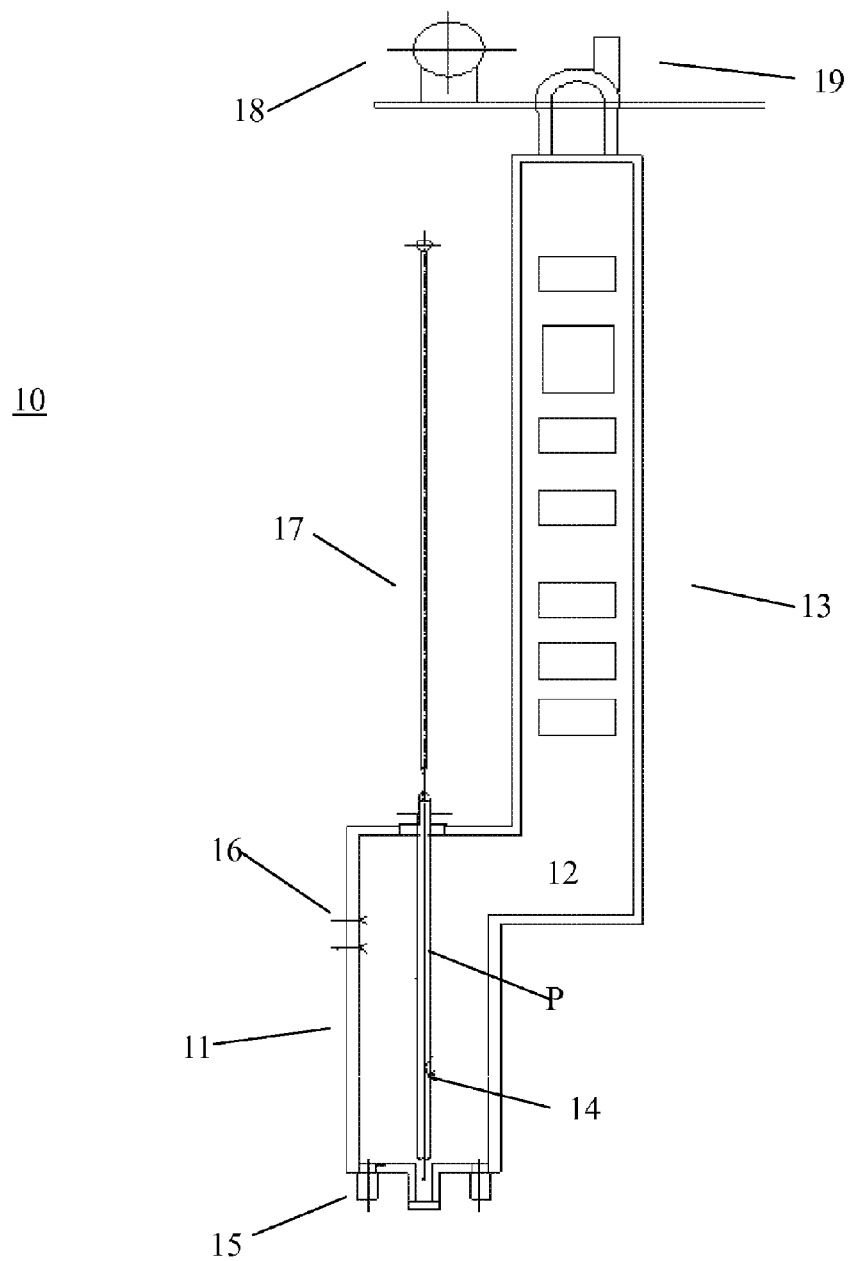
FIG. 1A shows a typical ethylene cracking furnace according to the prior art.
Figure 1B:
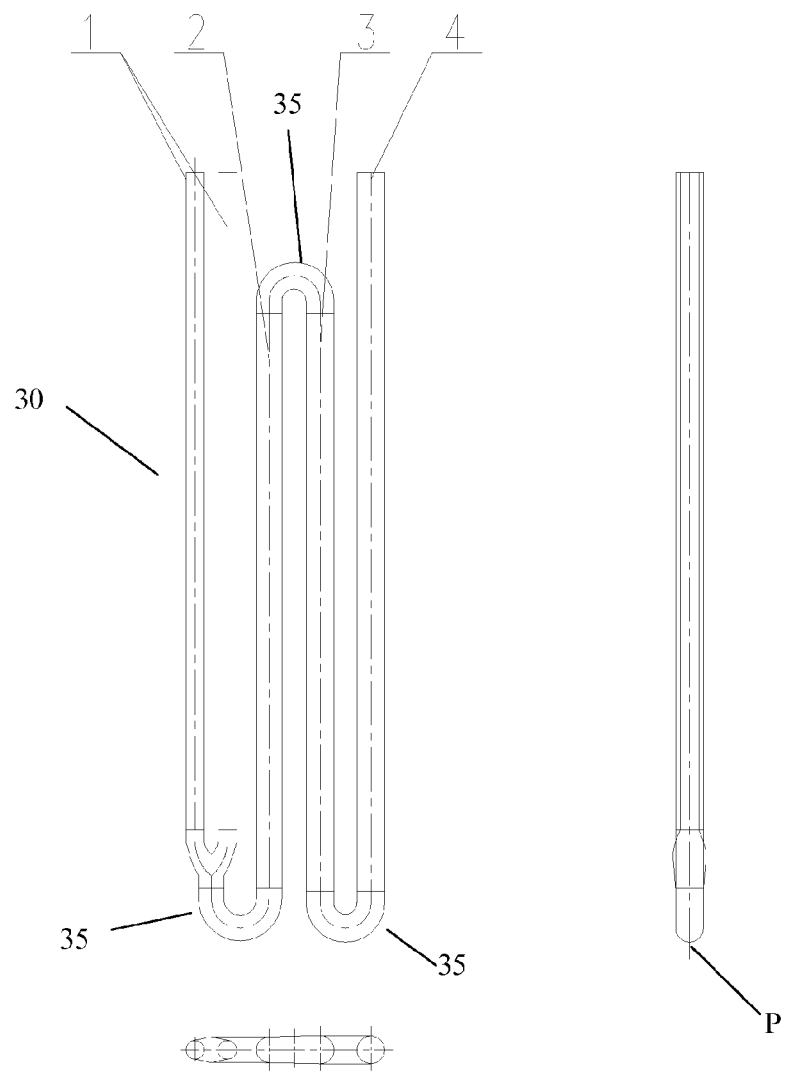
FIG. 1B shows a typical four-pass radiant coil structure according to the prior art.
Figure 2:
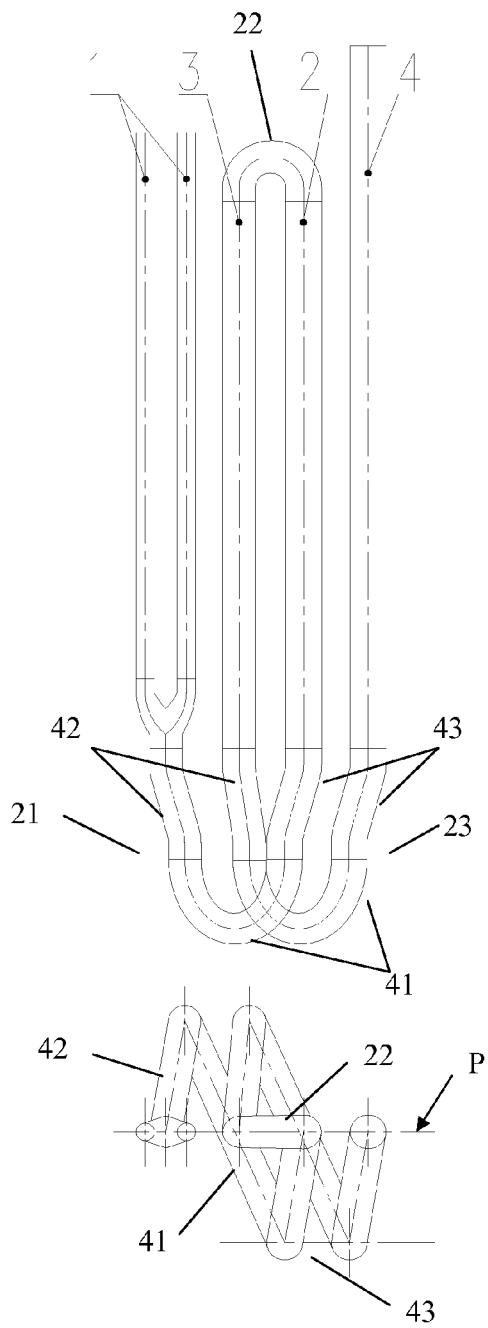

FIG. 2 shows the first embodiment of four-pass radiant coil according to the present invention, which can be used in the ethylene cracking furnace 10 shown in FIG. 1, for example. As shown in FIG. 2, along the flow direction of fluid the coil is divided into four passes, i.e., the first tube 1, the second tube 2, the third tube 3 and the fourth tube 4. The first tube 1, i.e., the inlet tube, is a Y-shaped branched tube with varied diameters, which is already known in the prior art. The last tube, i.e., the fourth tube 4, is the outlet tube. All tubes are connected with each other by means of connectors 21-23. In this context, the connector between the first tube and the second tube is referred to as connector 21, the connector between the second tube and the third tube is referred to as connector 22, and the connector between the third tube and the fourth tube is referred to as connector 23, and so on.

For convenience, the wall temperatures of the first tube 1, the second tube 2, the third tube 3 and the fourth tube 4 are defined as T1, T2, T3 and T4 respectively. It is readily understood that with the cracking reaction carried out, the temperatures of the tubes will be gradually increased along the flow direction, that is to say, T1<T2<T3<T4.

As shown, the first tube 1 and the fourth tube 4 are respectively placed at the opposite outer sides of the four-pass radiant coil. However, according to the first embodiment, the second tube 2 and the third tube 3 are spatially arranged so that the third tube 3 is placed between the first tube 1 and the second tube 2, while the second tube 2 is placed between the third tube 3 and the fourth tube 4. In this arrangement, the third tube 3 having a temperature of T3 is spatially adjacent to the first tube 1 having a temperature of T1 and the second tube 2 having a temperature of T2, but spatially spaced from the fourth tube 4 having a temperature of T4. That is to say, the temperature in the radiant section 11 is distributed as T1, T3, T2 and T4 from left to right. In view of the relationship of T1<T2<T3<T4, the arrangement can effectively reduce the uneven temperature distribution in the radiant section 11. In the meantime, since the third tube 3 is separated from the fourth tube 4 through the second tube 2, the thermal radiation from the third tube 3 and the fourth tube 4 with relative high temperatures can be absorbed so as to lower the wall temperatures of the third tube 3 and the fourth tube 4. Consequently, with the arrangement according to the present invention, the surface temperature of the radiant coil can be further lowered, and thus the lifetime of the coil and the operation cycle of the cracking furnace can be both extended.

In addition, because the wall temperatures of tubes in the multi-pass radiant coil are different from each other, thermal stress will be generated due to different thermal expansion between two adjacent tubes, which would undesirably influence on the lifetime of the coil. For this purpose, the connector 21 according to the present invention is designed as a combined connector, which consists of a U-shaped elbow 41 and two S-shaped elbows 42, 43 respectively placed at two ends of the U-shaped elbow 41. In this way, the thermal stress due to different thermal expansion of two adjacent tubes can be absorbed by the combined connector, so that bending of the tubes due to thermal stress is avoid, further extending the lifetime of the radiant coil and the operation cycle of the ethylene cracking furnace.

It should be noted that in this embodiment, the connector 22 connecting the second tube 2 and the third tube 3 in the upper part of the radiant section is still a common elbow. However, it is understood to one skilled in the art that the connector 22 of common elbow can also be replaced with a combined connector consisting of U-shaped elbow and S-shaped elbows as mentioned above, which still falls within the scope of the present invention.

As mentioned above, in the prior arts all tubes of the multi-pass radiant coil as well as the connectors thereof are disposed in the central plane P of the radiant section 11. In this structure, the temperature distribution in the radiant section is uneven because of the significant temperature difference caused by the tubes located relatively far away. In the first embodiment according to the present invention, all four tubes are still arranged in the central plane P of the radiant section. However, as shown in FIG. 2, the first S-shaped elbow 42 in the combined connector 21 connecting to the rear end (i.e., the lower end) of the first tube 1 extends from its front end (located in the central plane P) toward the rear part of the radiant section 11 (i.e., the upper part of the central plane P in the drawing), and connects at its rear end to one end of the U-shaped elbow 41 in the combined connector 21. From the rear part of the radiant section, the U-shaped elbow 41 runs angularly across the central plane P to the front part of the radiant section (the lower part of the central plane P in the drawing), and connects at the other end thereof to the second S-shaped elbow 43 in the combined connector 21. The second S-shaped elbow 43 runs toward the central plane P, with its downward projection in parallel with that of the first S-shaped elbow 42, and connects to the front end (i.e., the lower end) of the second tube 2 at its rear end which is located in the central plane P. The second tube 2 connects to the third tube 3 through the connector 22 located in the central plane P. The third tube 3, the combined connector 23 and the fourth tube 4 are arranged in a similar manner, in which all S-shaped elbows have downward projections in parallel with each other. In this manner, two S-shaped elbows are arranged in the front part and the rear part of the radiant section respectively. Therefore, the arrangement of two consecutive tubes being spatially non-adjacent can lead to a more even temperature distribution in the radiant section 11, and at the same time the distortion generated by thermal stress can be absorbed equably. Therefore, the surface temperature of tubes can be further reduced, and the lifetime of the radiant coil and the operation cycle of the ethylene cracking furnace can be extended.

It can be seen from the drawing that the structure of this type of four-pass radiant coil is very compact, which is advantageous for large cracking furnace.

Next, other embodiments of four-pass radiant coils according to the present invention will be described. For the sake of conciseness, in the following only the features or components or functions different from those mentioned above will be described, while the same or similar features or components or functions will be omitted.

Figure 3:
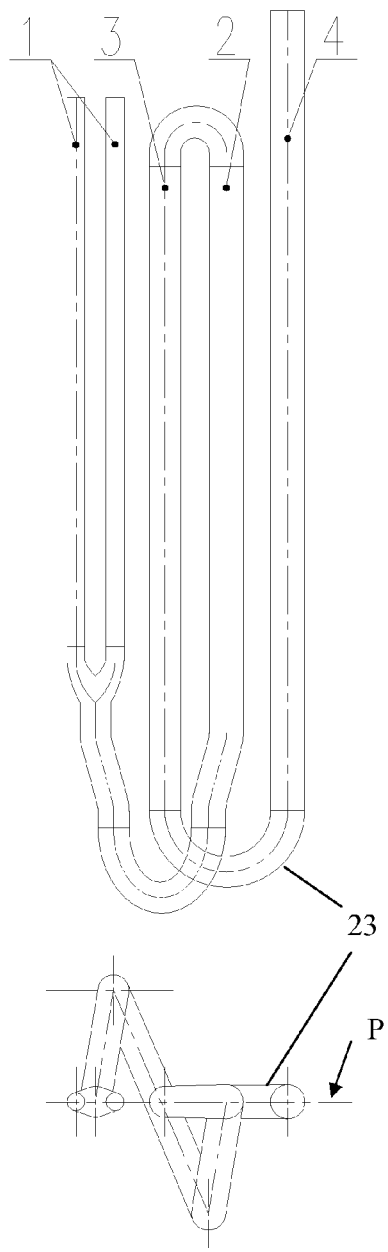

FIG. 3 shows the second embodiment of four-pass radiant coil according to the present invention. In this embodiment, the connector 23 for connecting the last two tubes, i.e., the third tube 3 and the fourth tube 4, is a traditional U-shaped elbow instead of the combined connector as shown in FIG. 2. In this way, the connector is also located in the central plane P of the radiant section. This arrangement as shown is structurally simpler than that in the first embodiment, and can be easily manufactured at low cost, which enables it suitable for some special cracking furnace.

FIGS. 4 and 5 show the third and the fourth embodiments of four-pass radiant coil according to the present invention respectively. The third and the fourth embodiments are generally the same as the first and the second embodiments respectively, except that the first tube 1 is a conventional non-branched tube with a constant diameter, instead of a branched tube with varied diameters. This arrangement may be advantageous for a certain cracking process and cracking furnace.

FIG. 6 shows the fifth embodiment of four-pass radiant coil according to the present invention, which is basically the same as the first embodiment. However, although the first tube 1, i.e., the inlet tube, is still placed at one of the outer sides of the radiant coil, the fourth tube 4, i.e., the outlet tube, is not placed at the other outer side as in the first embodiment, but is spatially closely adjacent to the first tube 1. As shown in FIG. 6, the tubes are arranged spatially in the radiant section 11 in an order of the first tube 1, the fourth tube 4, the second tube 2 and the third tube 3. In this way, the temperature of the tubes in the radiant section 11 is distributed as T1, T4, T2 and T3. Considering the relationship of T1<T2<T3<T4, the arrangement can also achieve the same effects as the first embodiment. In addition, since the fourth tube 4 having the highest temperature is located between the first and second tubes 1, 2 having the relatively lowest temperatures, the uneven temperature distribution is significantly suppressed.

FIGS. 7 to 9 show the sixth to the eighth embodiments of four-pass radiant coil according to the present invention respectively. The differences of the sixth to the eighth embodiments from the fifth embodiment correspond to those of the second to the fourth embodiments from the first embodiment respectively, which can be readily understood by one skilled in the art. Therefore, the detailed descriptions thereto are omitted here.

Six-Pass Radiant Coil

Figures 10, 11:
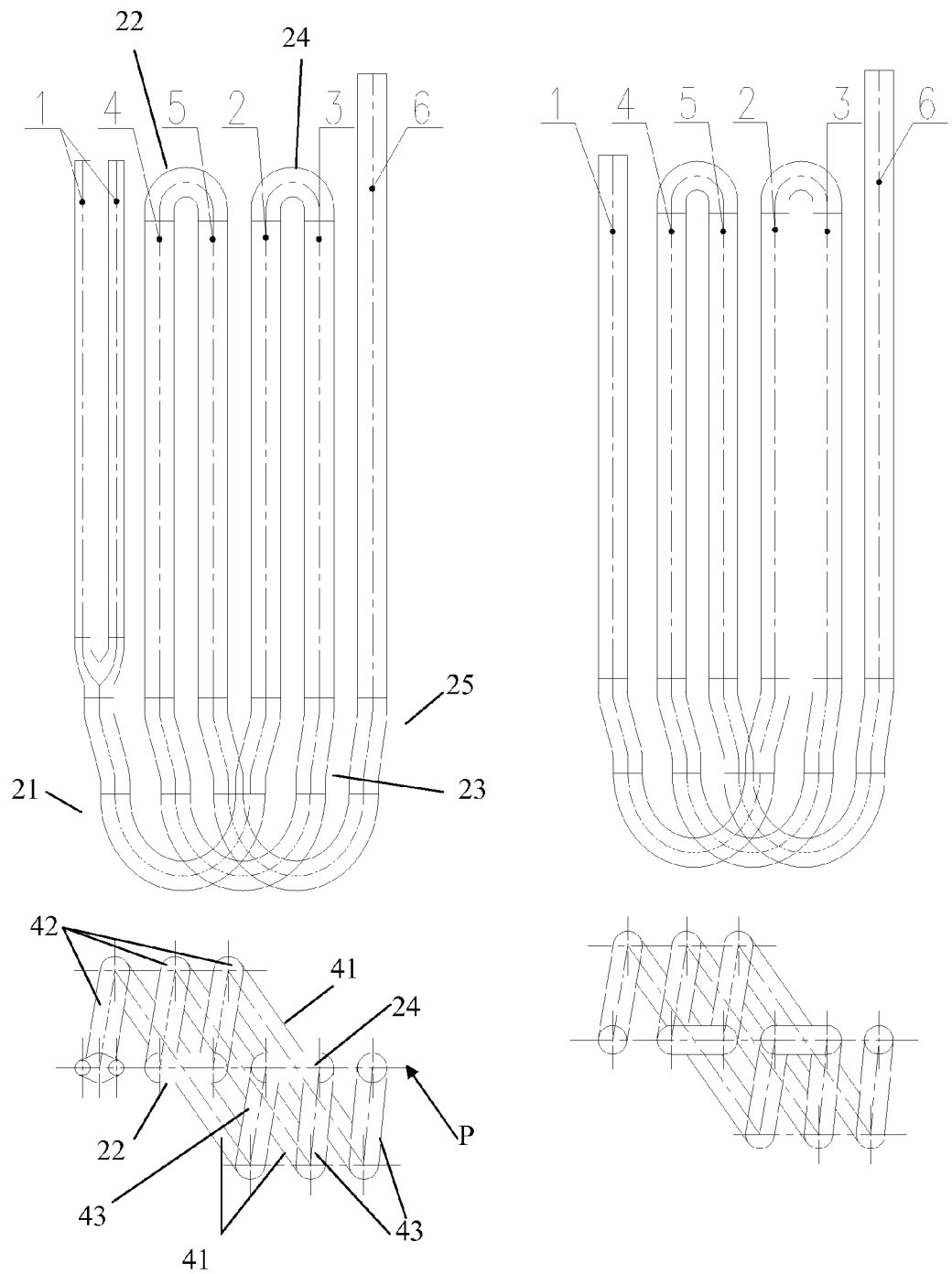

FIG. 10 shows the first embodiment of six-pass radiant coil according to the present invention, which can be used in, for example, the ethylene cracking furnace 10 of FIG. 1. As shown in FIG. 10, along the flow direction of fluid the coil is divided into the first tube 1, the second tube 2, the third tube 3, the fourth tube 4, the fifth tube 5 and the sixth tube 6. The first tube 1, i.e., the inlet tube, is a Y-shaped branched tube with varied diameters, while the last tube, i.e., the sixth tube 6, is the outlet tube. The tubes are connected with each other by means of connectors 21-25.

For better understanding, the tube wall temperatures in the first tube 1, the second tube 2, the third tube 3, the fourth tube 4, the fifth tube 5 and the sixth tube 6 are defined as T1, T2, T3, T4, T5 and T6 respectively. It is obviously understood that with the cracking reaction carried out, the temperatures in the tubes will be gradually increased along the flow direction, that is to say, T1<T2<T3<T4<T5<T6.

As shown in FIG. 10, the tubes are arranged so that they are spatially distributed in a sequence of the first tube 1, the fourth tube 4, the fifth tube 5, the second tube 2, the third tube 3 and the sixth tube 6. Therefore, the temperature distribution within the radiant section 11 is T1, T4, T5, T2, T3 and T6 from left to right. Because of the relationship of T1<T2<T3<T4<T5<T6, the arrangement can effectively reduce the uneven temperature distribution within the radiant section 11. At the same time, since the fifth tube 5 is spaced from the sixth tube 6 by means of the second tube 2 and the third tube 3, the heat radiation influence generated between the fifth tube 5 and the sixth tube 6 that have relatively high temperatures is avoided. Consequently, the arrangement according to the present invention can further lower the surface temperature of the radiant coil, thus extending the lifetime thereof and the operation cycle of the cracking furnace.

As in the first embodiment of four-pass radiant coil shown in FIG. 2, each of the connectors 21, 23 and 25 in the lower part of the radiant section 11 is designed as combined connector consisting of a U-shaped elbow and two S-shaped elbows that are disposed at the opposite outer sides of the U-shaped elbow respectively. Thus, the thermal stress generated between two consecutive tubes can be absorbed by the combined connector, thus avoiding the bending and partial overheating of tubes due to thermal stress. Therefore, the lifetime of the radiant coil and the operation cycle of the furnace can be further extended.

It should be noted that in this embodiment, the connectors 22, 24 in the upper part of the radian section 11 is still a common elbow. However, it is understood to one skilled in the art that the connectors 22, 24 of common elbow can also be designed as combined connector consisting of U-shaped elbow and S-shaped elbows as mentioned above, which still falls within the scope of the present invention.

In this embodiment, all six tubes of six-pass radiant coil are arranged in the central plane P of the radiant section. The first S-shaped elbow 42 of the combined connector 21 extends from its front end, which is in the central plane P and connects to the first tube 1, toward the rear part of the radiant section, i.e., the upper part over the central plane P in the drawing, and connects at its rear end to one end of the U-shaped elbow 41 of the combined connector 21. From the rear part of the radiant section, the U-shaped elbow 41 runs angularly across the central plane P to the front part of the radiant section, i.e., the lower part of the central plane P in the drawing, and connects at the other end thereof to the second S-shaped elbow 43 of the combined connector 21. The second S-shaped elbow 43 runs toward the central plane P with its downward projection in parallel with that of the first S-shaped elbow 42, and connects to the front end, i.e., the lower end, of the second tube 2 at its rear end which is located in the central plane P. The second tube 2 connects to the third tube 3 through the connector 22 located in the central plane P. The connection from the third tube 3 to the sixth tube 6, including the connectors, is similar as the foregoing, in which all S-shaped elbows have downward projections in parallel with each other. In this manner, three S-shaped elbows are respectively arranged in the front part and the rear part of the radiant section. The arrangement can lead to a more even temperature distribution in the radiant section 11, and at the same time the distortion generated by thermal stress can be absorbed equably. Therefore, the surface temperature of tubes can be further reduced, and the lifetime of the radiant coil and the operation cycle of the ethylene cracking furnace can be extended.

It can be seen from the drawing that the structure of this kind of six-pass radiant coil is very compact, which is advantageous for large cracking furnace.

Next, other embodiments of six-pass radiant coils according to the present invention will be described. For the sake of conciseness, in the following only the features or components or functions different from those having been disclosed in the foregoing will be described, while the same or similar features or components or functions will be omitted.

FIG. 11 shows the second embodiment of six-pass radiant coil according to the present invention. The second embodiment is generally the same as the first embodiment, except that the first tube 1 is a conventional non-branched tube with a constant diameter, instead of a branched coil with varied diameters.

Figure 12:
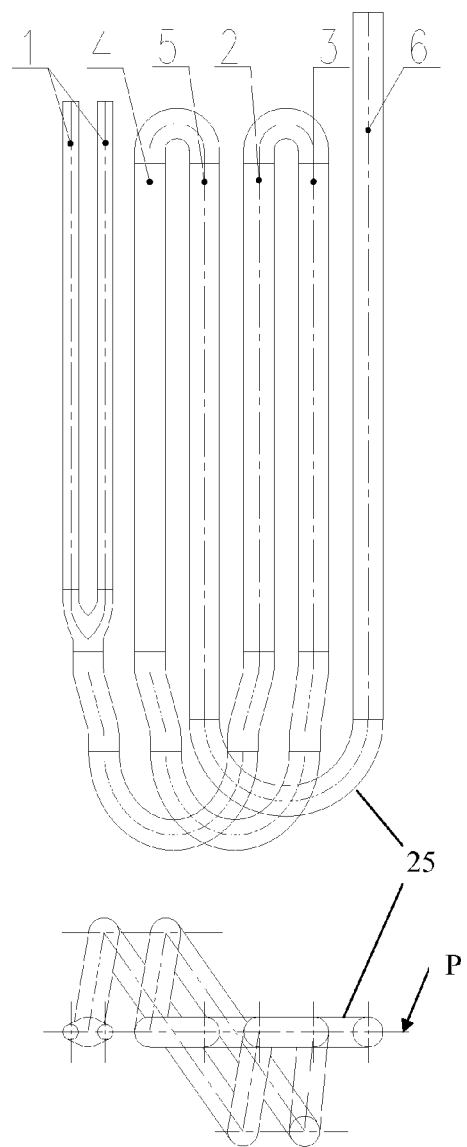

FIG. 12 shows the third embodiment of six-pass radiant coil according to the present invention. In this embodiment, the connector 25 for connecting the last two tubes, i.e., the fifth tube 5 and the sixth tube 6, is a traditional U-shaped elbow instead of the combined connector as shown in FIG. 10. In this way, the connector 25 is also located in the central plane P of the radiant section. This arrangement is structurally simpler than that in the first embodiment, and can be easily manufactured at low cost, which enables it suitable for some special cracking furnace.

Figure 13:
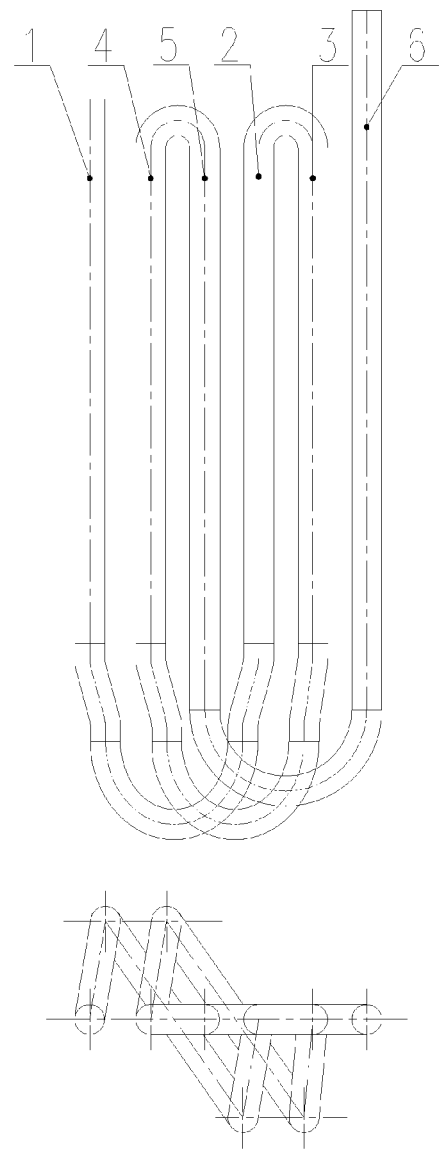

FIG. 13 shows the fourth embodiment of six-pass radiant coil according to the present invention. The fourth embodiment is generally the same as the third embodiment, except that the first tube 1 is a conventional non-branched tube with a constant diameter, instead of a branched tube with varied diameters.

FIG. 14 shows the fifth embodiment of six-pass radiant coil according to the present invention, which is basically the same as the first embodiment. However, although the first tube 1, i.e., the inlet tube, is still placed at one of the outer sides of the radiant coil, the sixth tube 6 is not placed at the other outer side as in the first embodiment, but is spatially closely adjacent to the first tube 1. As shown in FIG. 14, the tubes are arranged spatially in the radiant section 11 in an order of the first tube 1, the sixth tube 6, the third tube 3, the second tube 2, the fifth tube 5 and the fourth tube 4. In this way, the temperature of the tubes in the radiant section 11 is distributed as T1, T6, T3, T2, T5 and T4. In addition, the first tube 1, the third tube 3 and the sixth tube 6 are placed in the rear part of the radiant section, while the second tube 2, the fourth tube 4 and the fifth tube 5 are placed in the front part of the radiant section. Considering the relationship of T1<T2<T3<T4<T4<T5<T6 and the spatial configuration of tubes, the arrangement can achieve the same effects as the first embodiment, and also have a compact structure. In addition, since the sixth tube 6 having the highest temperature is located adjacent to the first tube 1 having the lowest temperatures, the uneven temperature distribution is significantly suppressed.

FIGS. 15 to 17 show the sixth to the eighth embodiments of six-pass radiant coil according to the present invention respectively. The differences of the sixth to the eighth embodiments from the fifth embodiment correspond to the differences of the second to the fourth embodiments from the first embodiment respectively, which can be readily understood by one skilled in the art. Therefore, the detailed descriptions thereto are omitted here.

FIG. 18 shows the ninth embodiment of six-pass radiant coil according to the present invention. In this embodiment, the tubes are arranged spatially in an order of the first tube 1, the sixth tube 6, the second tube 2, the third tube 3, the fifth tube 5 and the fourth tube 4. In other words, compared to the fifth embodiment, the spatial positions of the second tube 2 and the third tube 3 are exchanged with each other. Consequently, the sixth tube 6 having the highest temperature is located between the two tubes 1, 2 having the lowest temperature, and thus the uneven temperature distribution is significantly suppressed. It should be noted that in this arrangement, the first S-shaped elbow 42 of the last connector 25 has a downward projection not in parallel with those of other S-shaped elbows.

FIGS. 19 to 21 show the tenth to the twelfth embodiments of six-pass radiant coil according to the present invention respectively. The differences of the tenth to the twelfth embodiments from the ninth embodiment correspond to the differences of the second to the fourth embodiments from the first embodiment respectively, which can be readily understood by one skilled in the art. Therefore, the detailed descriptions thereto are omitted here.

Figure 22:
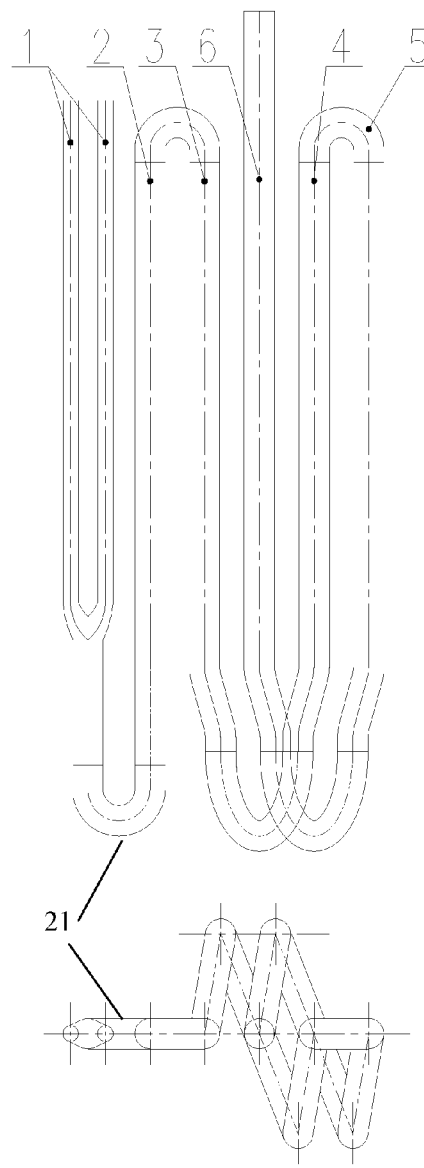

FIG. 22 shows the thirteenth embodiment of six-pass radiant coil according to the present invention. In this embodiment, the tubes are arranged spatially in an order of the first tube 1, the second tube 2, the third tube 3, the sixth tube 6, the fourth tube 4 and the fifth tube 5. In this design, the connector 21 for connecting the first tube 1 and the second tube 2 is a conventional elbow, which, together with other two connectors 22, 24, is located within the central plane P of the radiant section. The arrangement of the third to the sixth tubes is similar with those shown in FIG. 8. The structure of the thirteenth embodiment can be implemented in a relatively easy manner.

Figure 23:
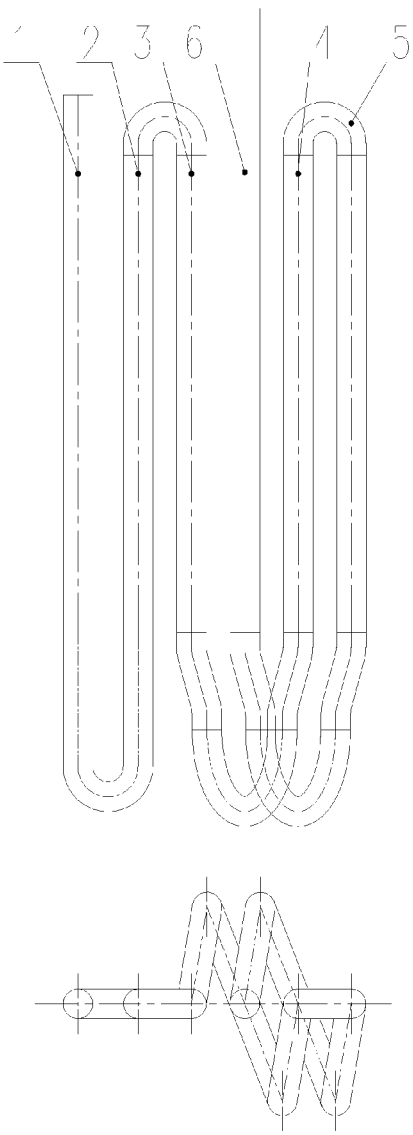

The fourteenth embodiment of six-pass radiant coil according to the present invention as shown in FIG. 23 differs from the thirteenth embodiment as shown in FIG. 22 only in that the first tube 1 is a non-branched conventional tube with a constant diameter.

The fifteenth embodiment of six-pass radiant coil according to the present invention as shown in FIG. 24 differs from the thirteenth embodiment as shown in FIG. 22 only in that the arrangement of the third to the sixth tubes are similar with that shown in FIG. 9.

The sixteenth embodiment of six-pass radiant coil according to the present invention as shown in FIG. 25 differs from the fifteenth embodiment as shown in FIG. 24 only in that the first tube 1 is a non-branched conventional tube with a constant diameter.

Figure 26:
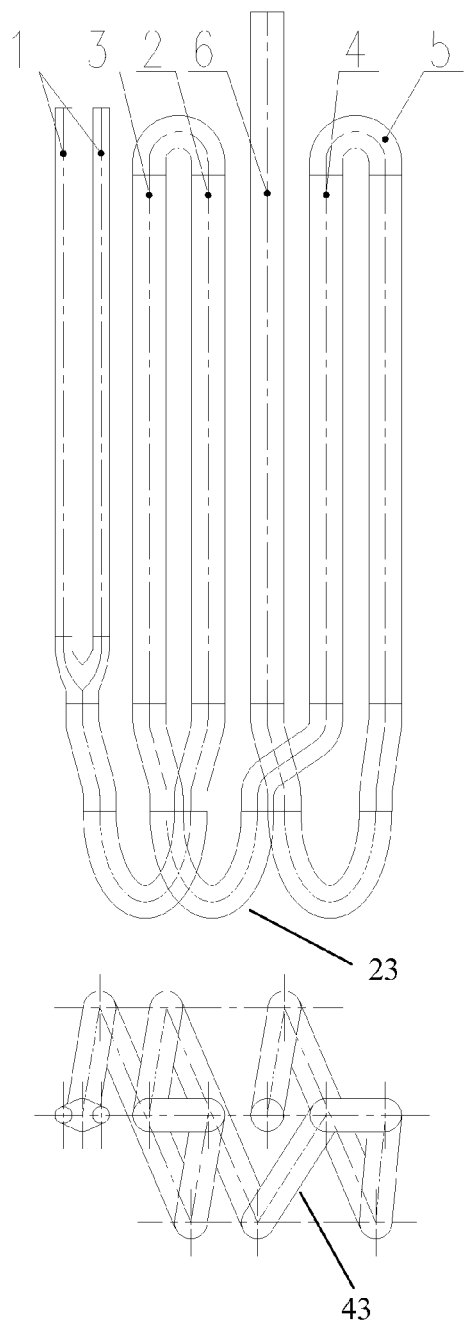

FIG. 26 shows the seventeenth embodiment of six-pass radiant coil according to the present invention. In this embodiment, the tubes are arranged spatially in an order of the first tube 1, the third tube 3, the second tube 2, the sixth tube 6, the fourth tube 4 and the fifth tube 5. In this design, three connectors 21, 23 and 25 located in the lower part of the radiant section are all combined connector. In view of structural reason, the second S-shaped elbow 43 of the connector 23 for connecting the third tube 3 and the fourth tube 4 has a downward projection not in parallel with that of other S-shaped elbows. As those mentioned above, the arrangement as shown can also achieve advantageous effects of lowering the surface temperature of tubes and extending the lifetime of the radiant coil and the operation cycle of the ethylene cracking furnace.

Figure 27:
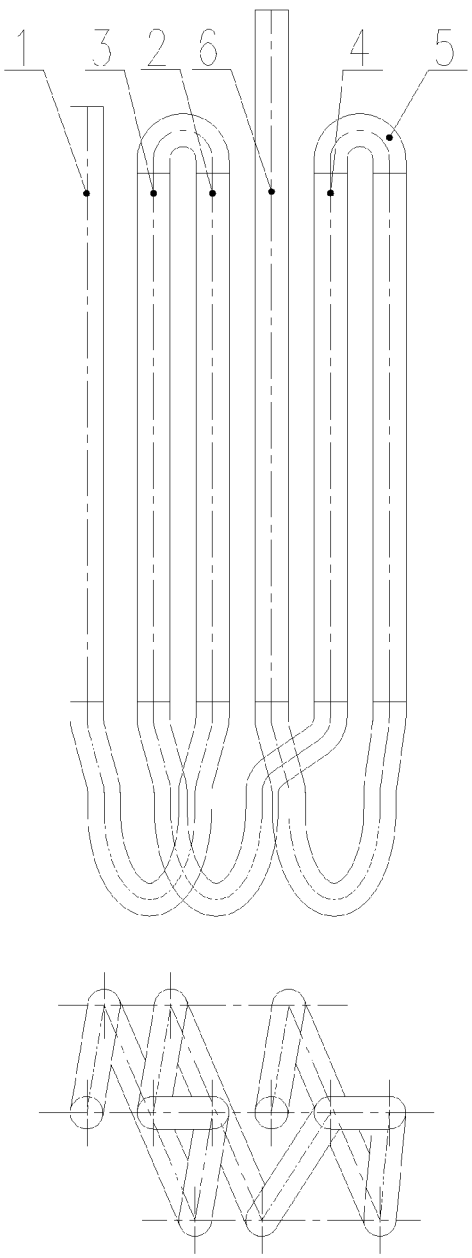

The eighteenth embodiment of six-pass radiant coil according to the present invention as shown in FIG. 27 differs from the seventeenth embodiment as shown in FIG. 26 only in that the first tube 1 is a non-branched conventional tube with a constant diameter.

The nineteenth embodiment of six-pass radiant coil according to the present invention as shown in FIG. 28 differs from the seventeenth embodiment as shown in FIG. 26 only in that the connector 25 for connecting the last two tubes, i.e., the fifth tube 5 and the sixth tube 6, is a U-shaped elbow located in the central plane P.

The twentieth embodiment of six-pass radiant coil according to the present invention as shown in FIG. 29 differs from the nineteenth embodiment as shown in FIG. 28 only in that the first tube 1 is a non-branched conventional tube with a constant diameter.

FIG. 30 shows the twenty-first embodiment of six-pass radiant coil according to the present invention. In this embodiment, both of the first tube 1 and the second tube 2 are Y-shaped branched tube with varied diameters. The tubes are arranged spatially in an order of the first tube 1, the second tube 2, the third tube 3, the fifth tube 5, the fourth tube 4 and the sixth tube 6.

As shown in FIG. 30, in the embodiment, the arrangement of the first to the third tubes is similar to that in FIG. 10, while the arrangement of the third to the sixth tubes is similar to that in FIG. 2. All S-shaped elbows have downward projections in parallel with each other, and all U-shaped elbows also have downward projections in parallel with each other.

FIG. 31 shows the twenty-second embodiment of six-pass radiant coil according to the present invention. It differs from the twenty-first embodiment only in that the arrangement of the third to the sixth tubes is similar to that in FIG. 3.

Figure 32:
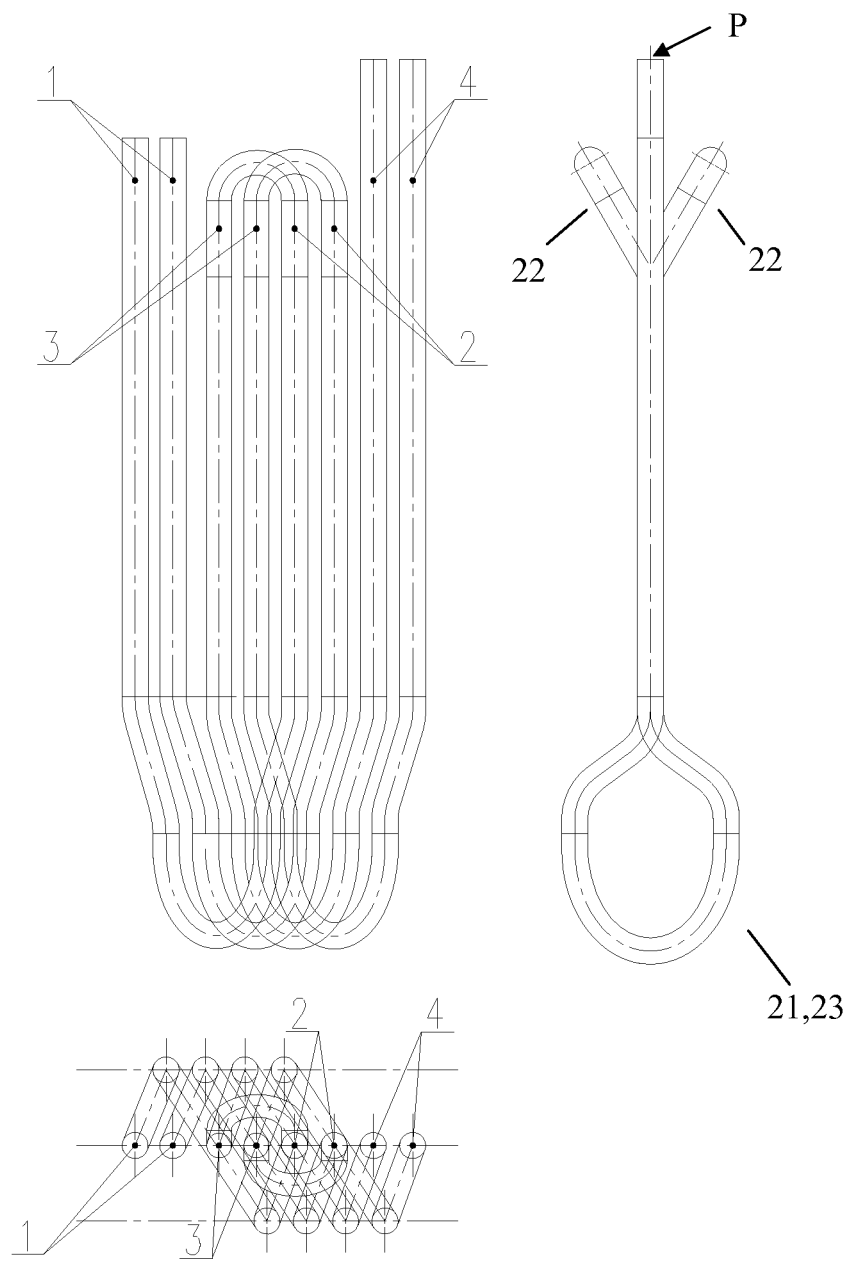
FIGS. 32-35 show four embodiments according to another aspect of the present invention, wherein the connectors for connecting the tubes form a profile of continuous curve in the side view.

FIG. 32 shows a structure of four-pass radiant coil according to the present invention, in which all tubes are arranged substantially in a manner as shown in FIG. 4. Here, two sets of coils are combined together, forming a structure of type 2-2-2-2.

In addition, each connector for connecting tubes in the lower part of the radiant section is still a combined connector consisting of U-shaped elbow and S-shapes elbows. However, as shown in the right half of the drawing (the left view), these combined connectors 21, 23 form a closed, smooth curve in the side view. This configuration enables the connectors can absorb the thermal stress generated in the radiant section more effectively.

Moreover, as shown in the left view, two connectors located at the upper part of the radiant section which are common elbows are no longer in the central plane P of the radiant section. Instead, the connectors are located in two planes that are mirror-symmetrical to each other about the central plane P and form an angular therewith respectively. This configuration is advantageous in the mechanical structure for hanging the radiant coil.

Figure 33:
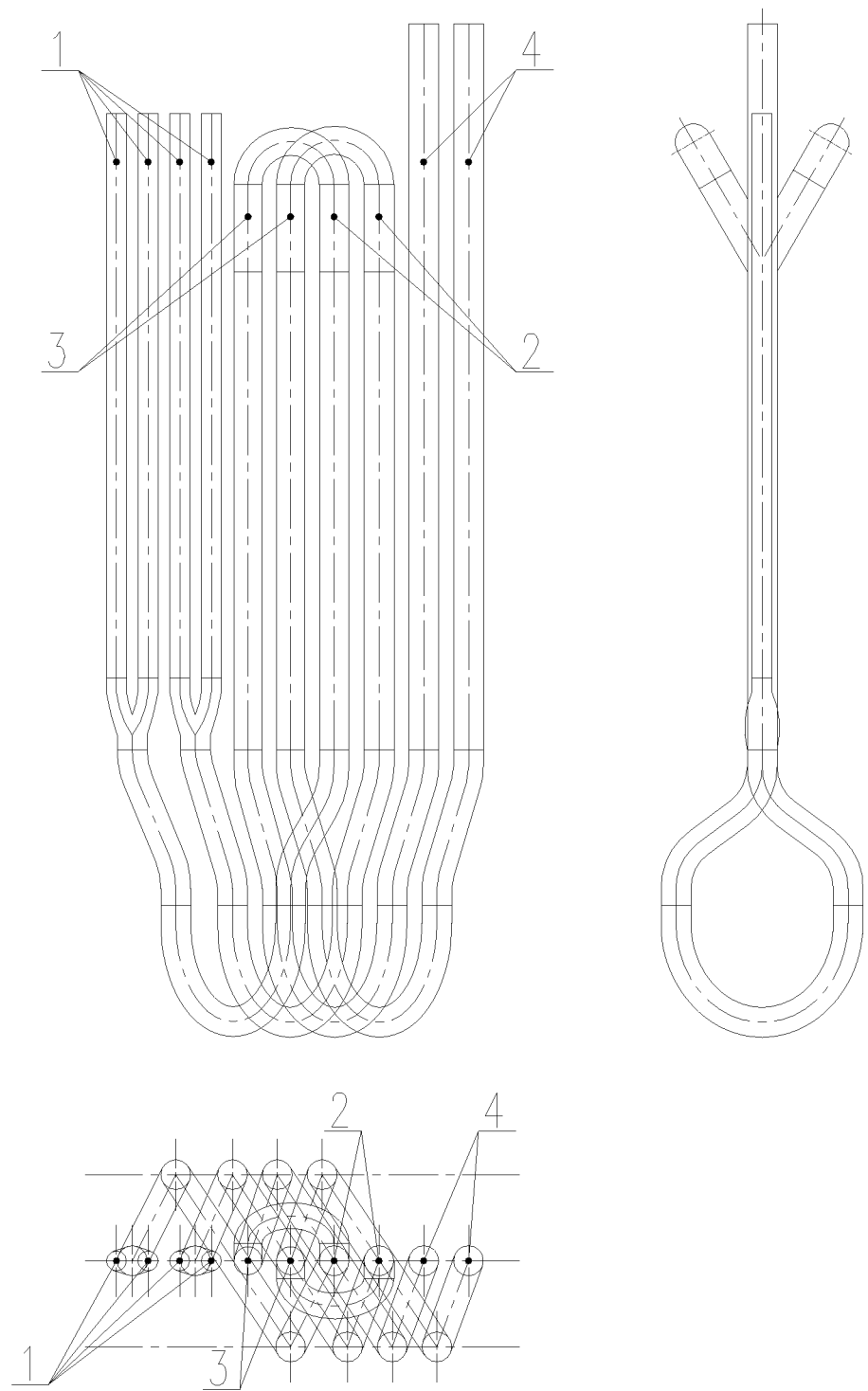

The structure shown in FIG. 33 is similar to that in FIG. 32, except that each sub-tube of the first tube 1 is of Y-shaped branched tube with varied diameters. All tubes are structured substantially as shown in FIG. 2 and has a combination of two sets of tubes combined together, forming a structure of type 4-2-2-2.

Figure 34:
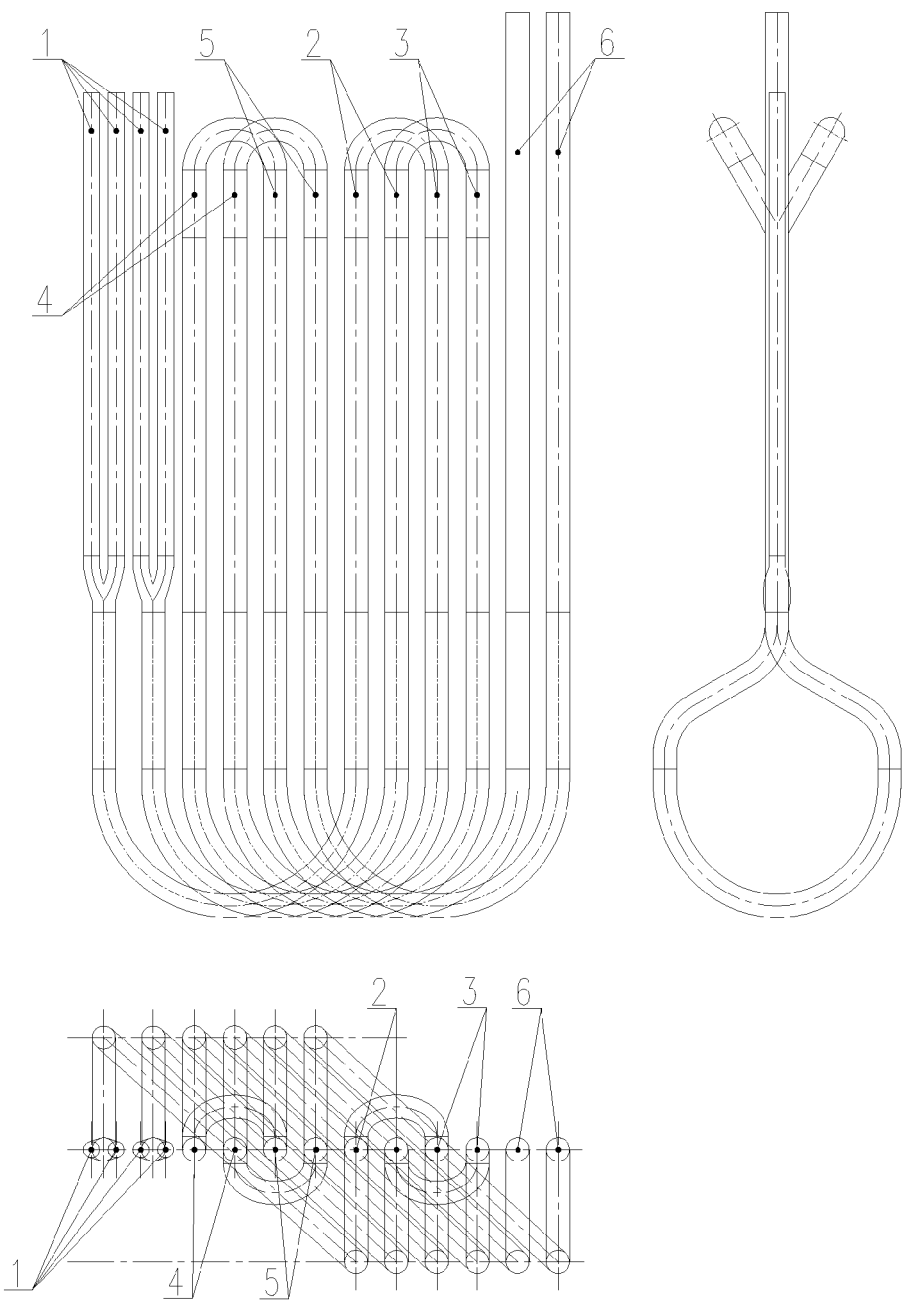

FIG. 34 shows a structure of six-pass radiant coil, in which each tube has a structure substantially as that of FIG. 10. It has a combination of two sets of tubes, forming a structure of type 4-2-2-2-2-2. However, the downward projection of S-shaped tubes is perpendicular to the central plane P.

Figure 35:
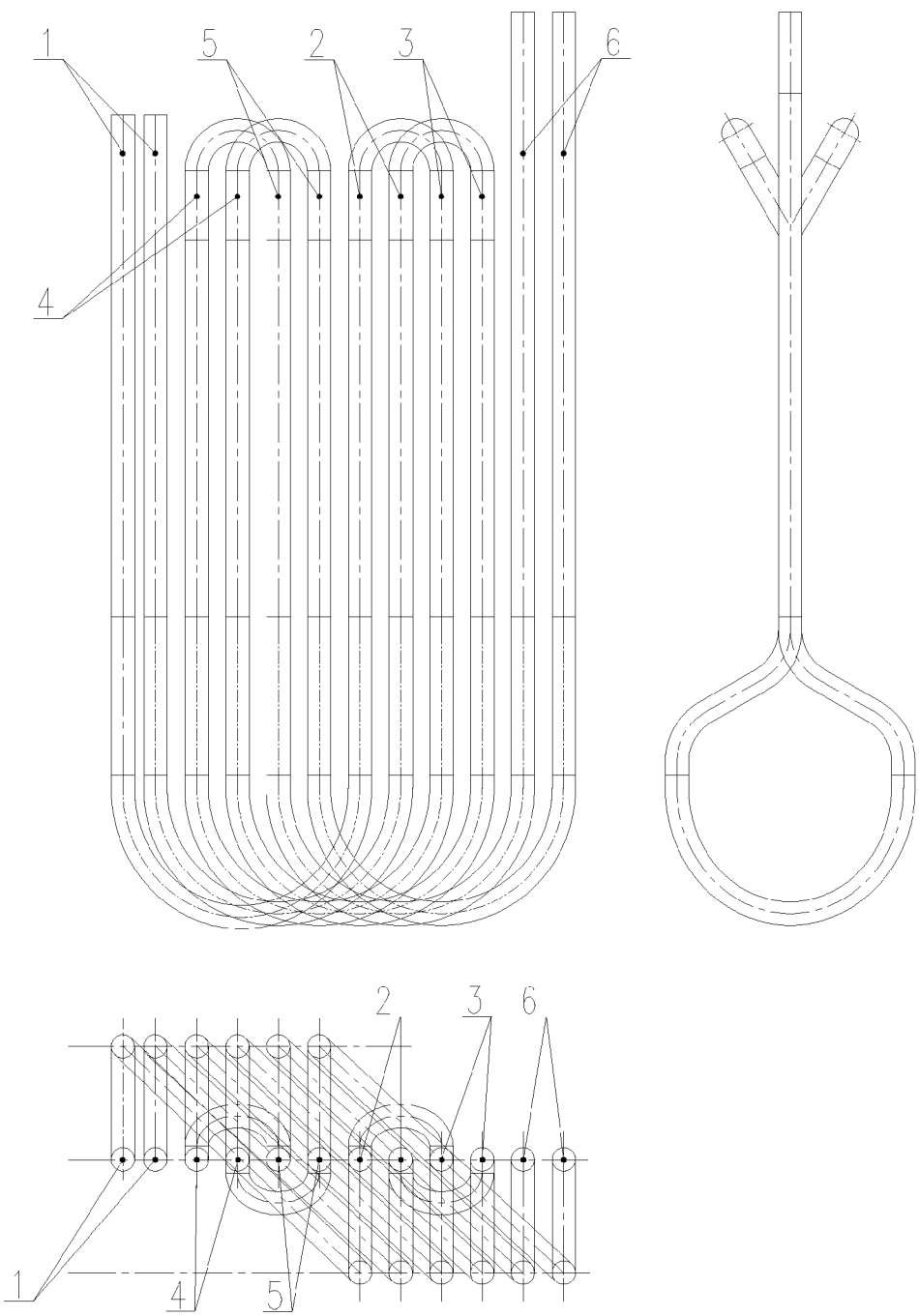

FIG. 35 shows a structure of six-pass radiant coil, in which each tube has a structure substantially as that of FIG. 11. It has a combination of two sets of tubes, forming a structure of type 2-2-2-2-2-2.

It should be noted that although in all embodiments mentioned above the first tube 1 is located at one of the outer sides of the multi-pass radiant coil for each case, the first tube 1 can also be placed in the middle of the multi-pass radiant coil, as the last tube 4 or 6.

In the foregoing the present invention is described with the examples of four- and six-pass radiant coils. However, it is readily understood that the structure disclosed here can be also applied for eight-pass, ten-pass, and even the radiant coil with more passes. One skilled of the art can easily conceive these variants after reading the present disclosure.

It would be obvious that in an embodiment not shown, all tubes can be a combination of two sets of tubes, i.e., forming a structure of type 2-2-2-2. In some other embodiments not shown, a structure of type 4-2-2-2 or a combination of more sets of tubes can be adopted.

Moreover, although in the foregoing the invention is described with reference to a set of radiant coil or two sets of radiant coils arranged in a cracking furnace, it is understood that more sets of radiant coil can be arranged in one single cracking furnace, dependent on the actual requirements. For the case that more than one set of radiant coil is arranged in one cracking furnace, they can be arranged in sequence. Alternatively, the sets of radiant coils can be arranged in form of manifolds. In this case, the last tube should be placed at one side of the coil, and the coils should be arranged in a mirror-symmetric way.

Although the invention is described in details with reference to some embodiments, it will be apparent to those skilled in the art that modifications and variations may be made to some features/components/structures of the present invention without departing from the spirit or scope of the invention. In particular, the features disclosed in one embodiment can be combined with those disclosed in other embodiments in arbitrary ways unless the combinations may cause conflicts. It is intended that the present invention covers all the modifications and variations thereof provided they come within the scope of the appended claims and their equivalents.

The invention claimed is:

1. An ethylene cracking furnace having multi-pass radiant coil, comprising at least one radiant section, which includes bottom burner and/or sidewall burner, and at least one multi-pass radiant coil arranged along the longitudinal direction of the radiant section,
   wherein the multi-pass radiant coil is one selecting from a group consisting of four-to ten-pass radiant coils; and
   at least one tube of the multi-pass radiant coil is arranged to be spatially adjacent to a tube which is not consecutive to said at least one tube.

2. The ethylene cracking furnace according to claim 1, wherein the last two tubes of the multi-pass radiant coil are arranged to be spatially non-adjacent to each other.

3. The ethylene cracking furnace according to claim 1, wherein the first tube and the last tube are arranged at the opposite outer sides of the multi-pass radiant coil, respectively.

4. The ethylene cracking furnace according to claim 1, wherein at least one of the first tube and the last tube is not arranged at the outer side of the multi-pass radiant coil.

5. The ethylene cracking furnace according to claim 1, wherein each tube is located in the central plane of the radiant section.

6. The ethylene cracking furnace according to claim 1, wherein the tubes are connected to each other with connectors.

7. The ethylene cracking furnace according to claim 6, wherein at least one connector in the lower part of the radiant section is a combined connector consisting of a U-shaped elbow and two S-shaped elbows located at the opposite sides of the U-shaped elbow, respectively.

8. The ethylene cracking furnace according to claim 7, wherein equal quantity of S-shaped elbows are arranged at the opposite sides with respect to the central plane of the radiant section.

9. The ethylene cracking furnace according to claim 8, wherein the downward projections of all S-shaped elbows are parallel to each other.

10. The ethylene cracking furnace according to claim 8, wherein at least one S-shaped elbow has a downward projection not parallel to those of other S-shaped elbows.

11. The ethylene cracking furnace according to claim 8, wherein the two S-shaped elbows connecting two ends of the U-shaped elbow have downward projections parallel to each other.

12. The ethylene cracking furnace according to claim 7, wherein all U-shaped elbows in the combined connectors have downward projections parallel to each other.

13. The ethylene cracking furnace according to claim 7, wherein the connectors not in form of combined connector are all placed in the central plane of the radiant section.

14. The ethylene cracking furnace according to claim 1, wherein the first tube is a branched tube with varied diameters, or both of the first and the second tubes are branched tubes with varied diameters.

15. The ethylene cracking furnace according to claim 6, wherein the connectors in the lower part of the radiant section form a closed, substantially smooth curve viewed from its side view.

16. The ethylene cracking furnace according to claim 1, comprising two or more sets of radiant coils, in which the connectors in the upper part of the radiant section are located within symmetric planes angularly crossing the central plane of the radiant section and in mirror relationship therebetween.

* * * * *

UNITED STATES PATENT AND TRADEMARK OFFICE
CERTIFICATE OF CORRECTION

PATENT NO. : 8,900,522 B2  
APPLICATION NO. : 13/504117  
DATED : December 2, 2014  
INVENTOR(S) : Xiou He et al.

Page 1 of 1

It is certified that error appears in the above-identified patent and that said Letters Patent is hereby corrected as shown below:

Title page

Item (73) Assignees:
Change "China Petroleum & Chemical Corporation, Beijing Institute of Chemical Industry" to
--China Petroleum & Chemical Corporation, Beijing Research Institute of Chemical Industry--

Item (86) PCT No.:
Change "PCT/CN2010/000170" to
--PCT/CN2010/001703--

Signed and Sealed this
First Day of December, 2015

Michelle K. Lee
*Director of the United States Patent and Trademark Office*